(12) United States Patent
Iyer et al.

(10) Patent No.: US 12,076,312 B2
(45) Date of Patent: Sep. 3, 2024

(54) REPURPOSING ANTI-ANDROGEN THERAPY FOR COVID-19 AND IMMUNOTHERAPY

(71) Applicant: Wisconsin Alumni Research Foundation, Madison, WI (US)

(72) Inventors: Gopal Iyer, Madison, WI (US); Albert Wang, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 17/692,376

(22) Filed: Mar. 11, 2022

(65) Prior Publication Data

US 2022/0288029 A1    Sep. 15, 2022

Related U.S. Application Data

(60) Provisional application No. 63/160,081, filed on Mar. 12, 2021.

(51) Int. Cl.
| | |
|---|---|
| *A61K 31/4166* | (2006.01) |
| *A61K 31/167* | (2006.01) |
| *A61K 31/277* | (2006.01) |
| *A61K 31/4155* | (2006.01) |
| *A61K 31/4439* | (2006.01) |
| *A61P 37/06* | (2006.01) |

(52) U.S. Cl.
CPC ........ *A61K 31/4166* (2013.01); *A61K 31/167* (2013.01); *A61K 31/277* (2013.01); *A61K 31/4155* (2013.01); *A61K 31/4439* (2013.01); *A61P 37/06* (2018.01)

(58) Field of Classification Search
CPC ................ A61K 31/167; A61K 31/277; A61K 31/4155; A61K 31/4166; A61K 31/4439; A61P 37/06
See application file for complete search history.

(56) References Cited

U.S. PATENT DOCUMENTS

| | | | | |
|---|---|---|---|---|
| 5,162,117 A | * | 11/1992 | Stupak | A61K 9/209 424/475 |
| 2005/0008961 A1 | * | 1/2005 | Takada | G03G 9/0819 430/108.1 |
| 2018/0064688 A1 | * | 3/2018 | Dervan | A61K 31/4166 |

OTHER PUBLICATIONS

Cadegiani et al (Abstract, Preprint from Research Square, Dec. 2020) (Year: 2020).*
Patel et al. (European society of Medical Oncology, Jul. 9, 2020 pp. 1419-1420) (Year: 2020).*
Cadegiani et al (Cureus 13 (2) Feb. 22, 2021, pp. 1-8) (Year: 2021).*

* cited by examiner

*Primary Examiner* — Savitha M Rao
(74) *Attorney, Agent, or Firm* — Boyle Fredrickson, S.C.

(57) ABSTRACT

Use of an AR antagonist, e.g., enzalutamide and other known AR antagonists, for reducing inflammatory genes of COVID-19 subjects is provided by the present invention. In other aspects, the present invention is directed to the use of an AR antagonist, e.g., the drug enzalutamide and other known AR antagonists, to treat lung cancer in a subject. In yet other aspects, the present invention is directed to an AR antagonist, e.g., the drug enzalutamide and other known AR antagonists, as an immunotherapy.

8 Claims, 16 Drawing Sheets
(13 of 16 Drawing Sheet(s) Filed in Color)
Specification includes a Sequence Listing.

SEQUENCE LISTING

```
<160> NUMBER OF SEQ ID NOS: 10

<210> SEQ ID NO 1
<211> LENGTH: 25
<212> TYPE: DNA
```

```
<213> ORGANISM: Artificial Sequence
<220> FEATURE:
<223> OTHER INFORMATION: Androgen Receptor siRNA

<400> SEQUENCE: 1
gucacaaaga uuucuuacca acuct                                         25

<210> SEQ ID NO 2
<211> LENGTH: 27
<212> TYPE: DNA
<213> ORGANISM: Artificial Sequence
<220> FEATURE:
<223> OTHER INFORMATION: Androgen Receptor siRNA

<400> SEQUENCE: 2
agaguuggua agaaaucuuu gugacua                                       27

<210> SEQ ID NO 3
<211> LENGTH: 25
<212> TYPE: DNA
<213> ORGANISM: Artificial Sequence
<220> FEATURE:
<223> OTHER INFORMATION: Androgen Receptor siRNA

<400> SEQUENCE: 3
cuuuugaccu gcuaaucaag ucaca                                         25

<210> SEQ ID NO 4
<211> LENGTH: 27
<212> TYPE: DNA
<213> ORGANISM: Artificial Sequence
<220> FEATURE:
<223> OTHER INFORMATION: Androgen Receptor siRNA

<400> SEQUENCE: 4
ugugacuuga uuagcagguc aaaagug                                       27

<210> SEQ ID NO 5
<211> LENGTH: 25
<212> TYPE: DNA
<213> ORGANISM: Artificial Sequence
<220> FEATURE:
<223> OTHER INFORMATION: Androgen Receptor siRNA

<400> SEQUENCE: 5
augaaagcac ugcuacucuu cagca                                         25

<210> SEQ ID NO 6
<211> LENGTH: 27
<212> TYPE: DNA
<213> ORGANISM: Artificial Sequence
<220> FEATURE:
<223> OTHER INFORMATION: Androgen Receptor siRNA

<400> SEQUENCE: 6
ugcugaagag uagcagugcu uucaugc                                       27

<210> SEQ ID NO 7
<211> LENGTH: 22
<212> TYPE: DNA
<213> ORGANISM: Artificial Sequence
<220> FEATURE:
<223> OTHER INFORMATION: Androgen Receptor primer

<400> SEQUENCE: 7
agtactgaat gacagccatc tg                                            22
```

-continued

```
<210> SEQ ID NO 8
<211> LENGTH: 17
<212> TYPE: DNA
<213> ORGANISM: Artificial Sequence
<220> FEATURE:
<223> OTHER INFORMATION: Androgen Receptor primer

<400> SEQUENCE: 8
caacaaccag cccgact                                                    17

<210> SEQ ID NO 9
<211> LENGTH: 23
<212> TYPE: DNA
<213> ORGANISM: Artificial Sequence
<220> FEATURE:
<223> OTHER INFORMATION: Ubiquitin C primer

<400> SEQUENCE: 9
ccttatcttg gatctttgcc ttg                                             23

<210> SEQ ID NO 10
<211> LENGTH: 20
<212> TYPE: DNA
<213> ORGANISM: Artificial Sequence
<220> FEATURE:
<223> OTHER INFORMATION: Ubiquitin C primer

<400> SEQUENCE: 10
gatttgggtc gcagttcttg                                                 20
```

REPURPOSING ANTI-ANDROGEN THERAPY FOR COVID-19 AND IMMUNOTHERAPY

CROSS-REFERENCE TO RELATED APPLICATIONS

This application claims the benefit of U.S. Provisional Application No. 63/160,081, filed Mar. 12, 2021, and hereby incorporated by reference.

STATEMENT REGARDING FEDERALLY SPONSORED RESEARCH OR DEVELOPMENT

NA

FIELD OF THE DISCLOSURE

The present invention relates generally to disease treatment of coronavirus disease-19 (COVID-19) inflammation and immunotherapy. In particular, the present invention is directed to (a) use of an Androgen Receptor (AR) antagonist, e.g., the drug enzalutamide and other known AR antagonists, in COVID-19 and lung cancer patients (b) methods of treating COVID-19 inflammation using such AR antagonist drugs, and (c) related immunotherapy methods using such AR antagonist drugs.

BACKGROUND OF THE INVENTION

Coronavirus disease-19 (COVID-19) induced by the virus SARS-CoV-2 results in mild to severe inflammatory symptoms. Disease severity is due to both the viral replication as well as host response to infection. The overwhelming immune response can result in cytokine release syndrome with an uncontrolled rapid release of pro-inflammatory cytokines leading to acute respiratory distress syndrome (ARDS) and multi-organ failure.

Multiple recent reports have indicated a more severe course of COVID-19 with higher rates of intensive care unit (ICU) admission and higher mortality rates in men compared to women, irrespective of age. The dichotomy of COVID-19 disease progression in males versus females is startling and attributed to X chromosome-linked immune surveillance genes.

Accordingly, dissecting gender differences in physiological diseases such as inflammation in oncology settings is vital to improve treatment options.

BRIEF SUMMARY OF THE INVENTION

The present invention is directed towards reducing inflammation in males using an Androgen Receptor (AR) antagonist and further using it in an immunotherapeutic setting. The present invention demonstrates that hormone signaling has non-endocrine-like function in tissues other than its production. The presently disclosed anti-androgen therapy would not be used as in the existing regimen as prescribed in prostate cancer. Rather, its administration and efficacy in shorter duration would be used for reducing inflammation and priming the lung environment for immunotherapy.

Increased mortality associated with COVID-19 in male patients may be due to crosstalk between AR signaling and activation of the immune response. The present inventors have established a direct link between AR signaling and IL-6 expression through AR antagonist, enzalutamide, and RNA interference studies. AR signaling in bronchoalveolar and other non-small cell lung carcinoma cells are sensitive to androgens. Disruption of AR expression with enzalutamide resulted in a significant decrease in IL-6 expression and increased MAF expression. Thus, enzalutamide may be used to dampen the IL-6 expression in COVID-19 patients.

Through reanalysis of public datasets of existing SARS-CoV-2 infected lung cells, increased IL-6 expression and decreased MAF expression was discovered. Modeling the regulatory network revealed that IL-6 is the most connected hub gene controlled through transcription factor c-MAF with concomitant activation of several cytokine pathways, in SARS-CoV-2 infected lung cells. Together, these findings suggest that enzalutamide may be useful in reducing inflammatory genes by disrupting AR signaling cascade in COVID-19 patient lungs.

The present invention provides a method of treating a lung inflammation in a subject, comprising administering an effective amount of an Androgen Receptor (AR) antagonist to the subject wherein AR expression is inhibited and whereby the inflammation is reduced in the subject.

The AR antagonist may be selected from a group consisting of enzalutamide, bicalutamide, apalutamide, flutamide, nilutamide, and darolutamide.

The AR antagonist may decrease IL6 expression.

The AR antagonist may increase MAF expression.

The AR antagonist may promote the expression of one or more checkpoint inhibitors selected from a group consisting of IL4 and IL13 that are capable of inhibiting IL6 expression. The AR antagonist may increase IL4 expression. The AR antagonist may increase IL13 expression.

The AR antagonist may be administered at a dose of 80 mg to 240 mg per day, or 120 mg to 240 mg per day, or 160 mg to 240 mg per day. In one embodiment, the AR antagonist may be administered at a dose of about 160 mg per day.

The AR antagonist may be administered orally for a duration of five to seven days or less than seven days. The AR antagonist may be administered through inhalation for a duration of less than seven days or less than six days or less than five days or less than four days or less than three days or less than two days.

The subject may have COVID-19 and the lung inflammation may comprise bronchial epithelial cells infected with SARS-CoV-2.

The subject may have lung cancer and the lung inflammation may comprise cells affected with lung cancer.

The subject may be male.

The prevent invention provides use of an Androgen Receptor (AR) antagonist for the manufacture of a pharmaceutical composition for alleviating a symptom associated with COVID-19 or lung cancer in a subject.

The pharmaceutical composition may be formulated as an oral dose comprising the AR antagonist and a carrier.

The symptom associated with COVID-19 or lung cancer in the subject is lung inflammation.

The present invention provides an Androgen Receptor (AR) antagonist for use in alleviating a symptom associated with COVID-19 or lung cancer in a subject.

The AR antagonist may be formulated as an oral dose comprising the AR antagonist and a carrier.

The symptom associated with COVID-19 or lung cancer is lung inflammation.

The AR antagonist is selected from a group consisting of enzalutamide, bicalutamide, apalutamide, flutamide, nilutamide, and darolutamide.

Other objects, features and advantages of the present invention will become apparent after review of the specification, claims and drawings.

BRIEF DESCRIPTION OF THE DRAWINGS

The patent or application file contains at least one drawing executed in color. Copies of this patent or patent application publication with color drawings will be provided by the Office upon request and payment of the necessary fee.

The disclosure will be better understood and features and aspects beyond those set forth above will become apparent when considering the following detailed description. The detailed description makes reference to the following figures.

DETAILED DESCRIPTION OF THE INVENTION

I. In General

Figure 1A:
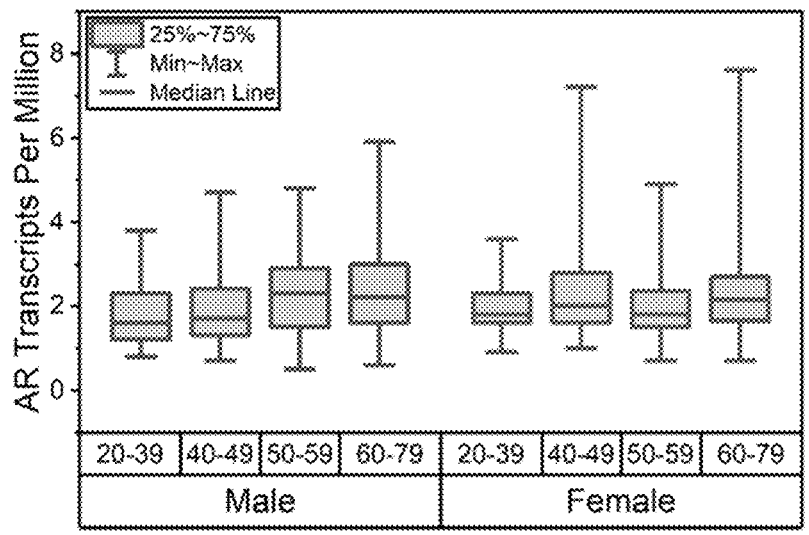
FIGS. 1A-1F shows Androgen Receptor (AR) expression in normal lung and lung cancer cell lines and response to enzalutamide. 1A, AR mRNA expression from 427 normal lung samples at different ages and genders. 1B, R1881 stimulation at 1 nM results in decrease of AR mRNA levels in A549 at 2, 4, 8 and 24 h time points when compared to control (±2SE and two-sample t-test: *P<0.05, P<0.01, *P<0.001). 1C, Comparison of AR mRNA levels in three conditions of enzalutamide treatment: enzalutamide alone (red), pre-treated with enzalutamide for 30 min prior to induction of 1 nM R1881 (blue), and pre-treated with R1881 for 30 min prior to enzalutamide treatment (green). 1D, Half maximal effective concentration (EC50) of enzalutamide treatment on lung cancer cells at 72 h. 1E, Representative immunofluorescent images of AR proteins in A549 treated with 1 nM R1881, 5 µM Enzalutamide (with or without 1 nM R1881), or AR siRNA (scale bar: 10 µm). 1F, Ratio of quantified AR immunofluorescent signals within the nucleus to the entire cell region (A549).

It is understood that this disclosure is not limited to the particular methodology, protocols, materials, and reagents described, as these may vary. The terminology used herein is for the purpose of describing particular embodiments only, and is not intended to limit the scope of the present invention, which will be limited only by any later-filed nonprovisional applications.

As used herein and in the appended claims, the singular forms "a", "an", and "the" include plural reference unless the context clearly dictates otherwise. As well, the terms "a" (or "an"), "one or more" and "at least one" can be used interchangeably herein. The terms "comprising" and variations thereof do not have a limiting meaning where these terms appear in the description and claims. Accordingly, the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, instruments, statistical analysis and methodologies which are reported in the publications which might be used in connection with the invention. All references cited in this specification are to be taken as indicative of the level of skill in the art.

The terminology as set forth herein is for description of the embodiments only and should not be construed as limiting of the invention as a whole. Unless otherwise specified, "a," "an," "the," and "at least one" are used interchangeably and mean one or more than one.

The disclosure is inclusive of the compounds described herein (including intermediates) in any of their pharmaceutically acceptable forms, including isomers (e.g., diastereomers and enantiomers), tautomers, salts, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

"Pharmaceutically acceptable" as used herein means that the compound or composition or carrier is suitable for administration to a subject to achieve the treatments described herein, without unduly deleterious side effects in light of the necessity of the treatment.

The term "effective amount," as used herein, refers to the amount of the compounds or dosages that will elicit the biological or medical response of a subject, tissue or cell that is being sought by the researcher, veterinarian, medical doctor or other clinician.

As used herein, "pharmaceutically-acceptable carrier" includes any and all dry powder, solvents, dispersion media, coatings, antibacterial and antifungal agents, isotonic agents, absorption delaying agents, and the like. Pharmaceutically-acceptable carriers are materials, useful for the purpose of administering the compounds in the method of the present invention, which are preferably non-toxic, and may be solid, liquid, or gaseous materials, which are otherwise inert and pharmaceutically acceptable, and are compatible with the compounds of the present invention. Examples of such carriers include, without limitation, various lactose, mannitol, oils such as corn oil, buffers such as PBS, saline, polyethylene glycol, glycerin, propylene glycol, dimethylsulfoxide, an amide such as dimethylacetamide, a protein such as albumin, and a detergent such as Tween 80, mono- and oligopolysaccharides such as glucose, lactose, cyclodextrins and starch.

The term "administering" or "administration," as used herein, refers to providing the compound or pharmaceutical composition of the invention to a subject suffering from or at risk of the diseases or conditions to be treated or prevented.

A route of administration in pharmacology is the path by which a drug is taken into the body. Routes of administration may be generally classified by the location at which the substance is applied. Common examples may include oral and intravenous administration. Routes can also be classified based on where the target of action is. Action may be topical (local), enteral (system-wide effect, but delivered through the gastrointestinal tract), or parenteral (systemic action, but delivered by routes other than the GI tract), via lung by inhalation.

A topical administration emphasizes local effect, and substance is applied directly where its action is desired. Sometimes, however, the term topical may be defined as applied to a localized area of the body or to the surface of a body part, without necessarily involving target effect of the substance, making the classification rather a variant of the classification based on application location. In an enteral administration, the desired effect is systemic (non-local), substance is given via the digestive tract. In a parenteral administration, the desired effect is systemic, and substance is given by routes other than the digestive tract.

Non-limiting examples for topical administrations may include epicutaneous (application onto the skin), e.g., allergy testing or typical local anesthesia, inhalational, e.g. asthma medications, enema, e.g., contrast media for imaging of the bowel, eye drops (onto the conjunctiva), e.g., antibiotics for conjunctivitis, ear drops, such as antibiotics and corticosteroids for otitis externa, and those through mucous membranes in the body.

Enteral administration may be administration that involves any part of the gastrointestinal tract and has systemic effects. The examples may include those by mouth (orally), many drugs as tablets, capsules, or drops, those by gastric feeding tube, duodenal feeding tube, or gastrostomy, many drugs and enteral nutrition, and those rectally, various drugs in suppository.

Examples of parenteral administrations may include intravenous (into a vein), e.g. many drugs, total parenteral nutrition intra-arterial (into an artery), e.g., vasodilator drugs in the treatment of vasospasm and thrombolytic drugs for treatment of embolism, intraosseous infusion (into the bone marrow), intra-muscular, intracerebral (into the brain parenchyma), intracerebroventricular (into cerebral ventricular system), intrathecal (an injection into the spinal canal), and subcutaneous (under the skin). Among them, intraosseous infusion is, in effect, an indirect intravenous access because the bone marrow drains directly into the venous system. Intraosseous infusion may be occasionally used for drugs and fluids in emergency medicine and pediatrics when intravenous access is difficult.

As used herein, the term "intraperitoneal injection" or "IP injection" refers to the injection of a substance into the peritoneum (body cavity). IP injection is more often applied to animals than to humans. In general, IP injection may be preferred when large amounts of blood replacement fluids are needed, or when low blood pressure or other problems prevent the use of a suitable blood vessel for intravenous injection.

II. The Invention

In certain aspects, the present invention is directed to the use of an AR antagonist, e.g., enzalutamide and other known AR antagonists, for reducing inflammatory genes of COVID-19 subjects. In other aspects, the present invention is directed to the use of an AR antagonist, e.g., the drug enzalutamide and other known AR antagonists, to treat lung cancer in a subject. In yet other aspects, the present invention is directed to an AR antagonist, e.g., the drug enzalutamide and other known AR antagonists, as an immunotherapy. Substitutes for enzalutamide include the following known AR antagonists:

1. Casodex—Generic Name—Bicalutamide
   a. Binds to the ligand binding domain of AR (https://www.ncbi.nlm.nih.gov/pmc/articles/PMC3788593/)
   b. First generation antagonist (reversible inhibitors that binds to AR with low affinity relative to androgens and offer incomplete transcriptional inhibition)
2. Xtandi—Generic Name—Enzalutamide
   a. Binds to AR with 5- to 8-fold greater affinity compared to bicalutamide (https://www.ncbi.nlm.nih.gov/pmc/articles/PMC3788593/)
   b. Second generation antagonist
3. Erleada—Generic Name—Apalutamide
   a. Binds to the ligand binding domain of the AR with 7- to 10-fold greater affinity compared with bicalutamide in LNCaP cells (https://www.ncbi.nlm.nih.gov/pmc/articles/PMC6643296/)
4. Eulexin—Generic Name—Flutamide
   a. Binds to the ligand binding domain of AR (https://www.ncbi.nlm.nih.gov/pmc/articles/PMC3788593/)
   b. First generation antagonist (reversible inhibitors that binds to AR with low affinity relative to androgens and offer incomplete transcriptional inhibition)
5. Nilandron—Generic Name—Nilutamide
   a. Binds to the ligand binding domain of AR (https://www.ncbi.nlm.nih.gov/pmc/articles/PMC3788593/)
   b. First generation antagonist (reversible inhibitors that binds to AR with low affinity relative to androgens and offer incomplete transcriptional inhibition)
6. Nubeqa—Generic Name—Darolutamide
   a. 8-fold greater affinity for AR compared with enzalutamide (https://www.ncbi.nlm.nih.gov/pmc/articles/PMC6643296/)
   b. Remains antagonistic against mutant AR forms (F877L mutation that confer resistance to enzalutamide)

A. Background

The present inventors recognize that disproportionately worse clinical outcomes observed in men may depend on alterations in androgen signaling in the lungs. While traditionally not considered an androgen-regulated tissue, there are several reports indicating the presence of Androgen Receptor (AR) protein and androgen-dependent gene expression in lung tissue. Specifically, the androgen signaling axis plays a crucial role in fetal lung development; and in adult lung tissue, AR is expressed in type II pneumocytes, bronchial epithelium, and airway smooth muscle. AR has also been linked to inflammatory responses, including IL6 signaling in prostate cancer. Intriguingly, recent data suggests that the COVID-19 mortality rate of men with prostate cancer treated with androgen deprivation therapy may be lower than those not receiving androgen deprivation therapy. Reducing the inflammatory response leading to acute respiratory distress syndrome (ARDS) in COVID-19 patients through inhibition of AR signaling is an attractive therapeutic paradigm since AR antagonists are well tolerated and have been used in millions of patients worldwide.

To provide further support for this conceptual advance towards implementing anti-androgen therapy in COVID-19 settings, the inventors confirmed that the inhibition of AR expression is intimately tied to anti-inflammatory response using clinically approved antagonist, e.g., enzalutamide and other known AR antagonists, in lung cancer cell lines. The inventors also established using a combination of AR perturbation in lung tissue using both in vitro experiments and publicly available studies. Specifically, the inventors perturbed AR expression in vitro using both pharmacologic and genetic approaches to examine the impact of AR modulation on gene expression in lung cancer cell lines (A549 and NCI-H2228). The inventors then used publicly available datasets of gene expression profiles from SARS-CoV-2 infected lung cells to establish potential connections between AR inhibition and SARS-CoV-2 infection in the lung. The results provide evidence that AR antagonism may be an attractive treatment approach to decrease expression of inflammatory genes in COVID-19 patients.

A large public database of 427 normal human lung samples was examined to determine mRNA expression of AR in normal lung. Expression of AR ranged from 1-7 transcripts per million (TPM) in both men and women with levels not varying by gender or age (FIG. 1a). This is consistent with findings from others, which show AR to be expressed in a normal lung and suggests that differences in AR expression itself is unlikely to explain disease severity.

Figure 1B:
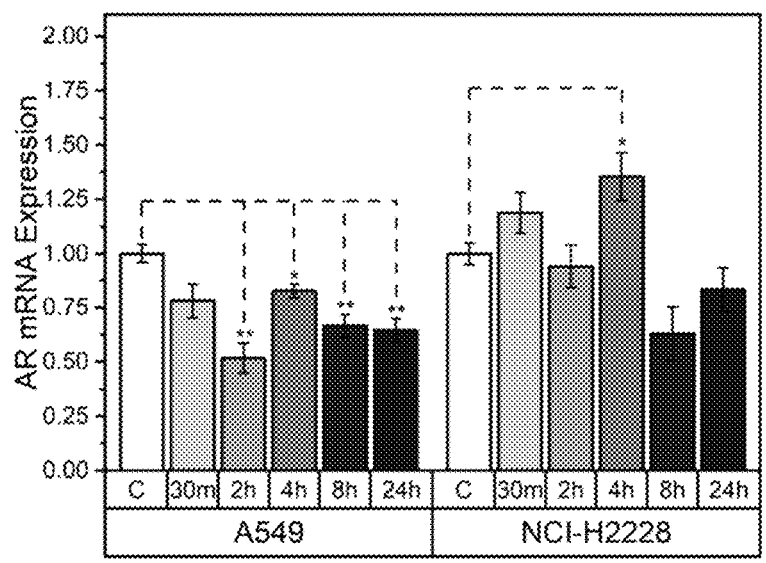
Figure 1C:
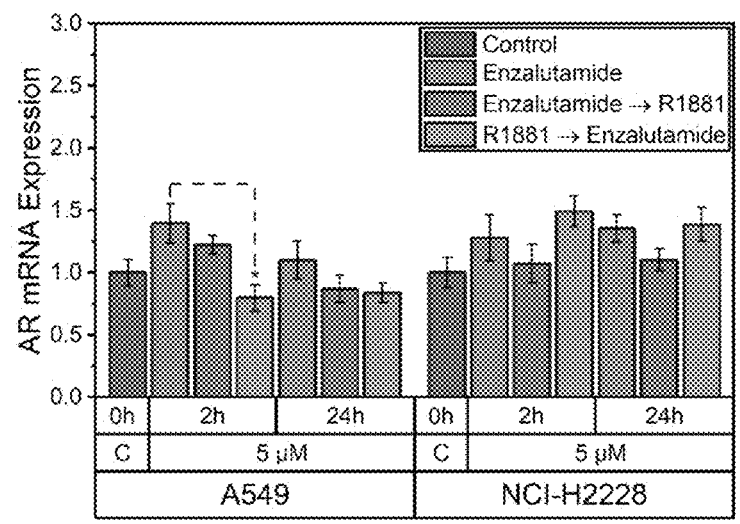
Figure 5:
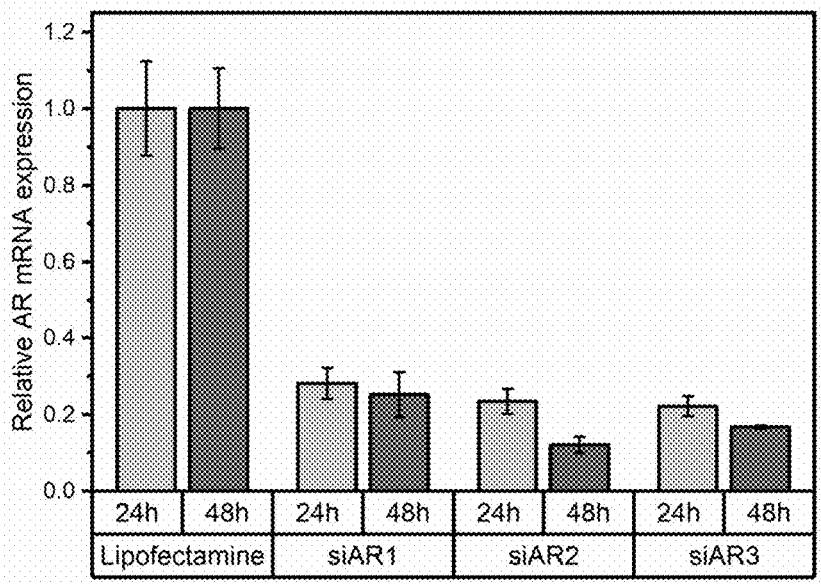
FIG. 5 shows AR siRNA transfection optimization. Three different siRNA sequences were tested for effectiveness of AR mRNA degradation. A549 cells were transfected with individual sequences at 10 nM concentration using lipofectamine for 24 h and 48 h. The mRNA samples were extracted, and the AR mRNA levels were measured with qRT-PCR. Data is presented as fold change±SE.
Figure 6A:
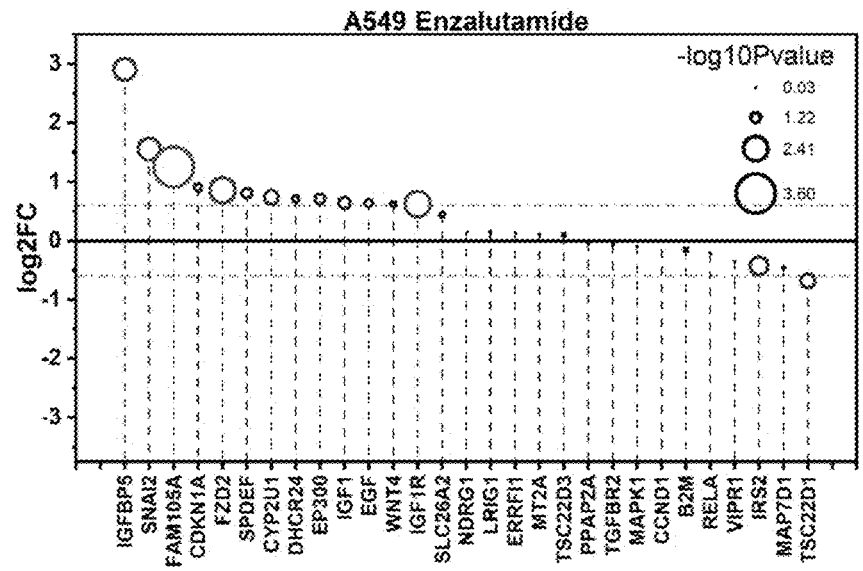
FIGS. 6A-6D shows gene expressions of A549 and H2228 in AR signaling panel, related to FIGS. 2A-2D. Log 2 fold change (log 2FC) gene expressions of enzalutamide treated A549 were obtained from AR signaling panels. Genes with absolute values of log 2FC greater than 0.6 (represented by horizontal grey dash-dotted lines) and p-value less than 0.05 (or 1.3 in −log 10 scale) are considered significant. The size and color (black to red) of the circle represent p-values.
Figure 6B:
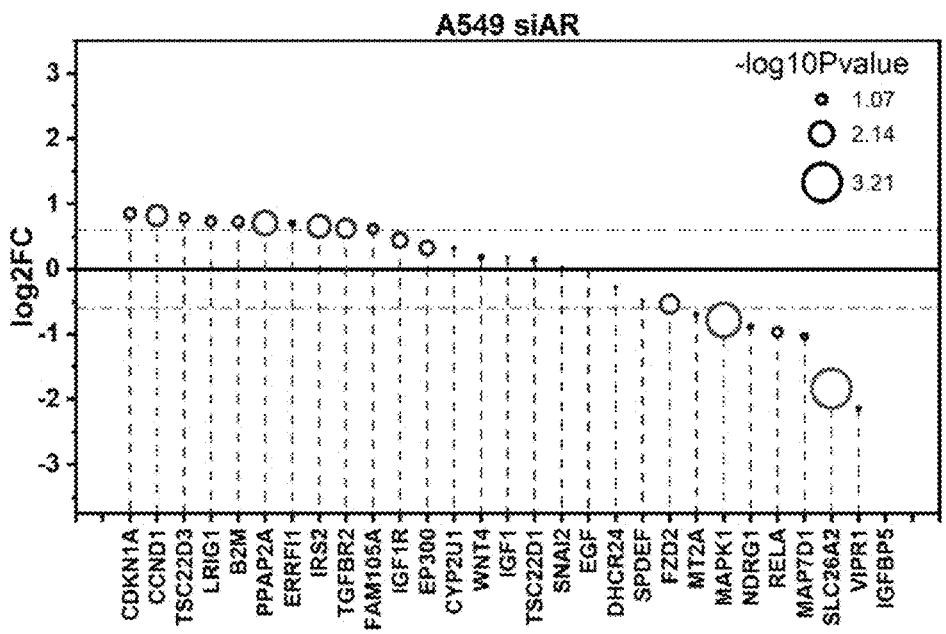
Figure 6C:
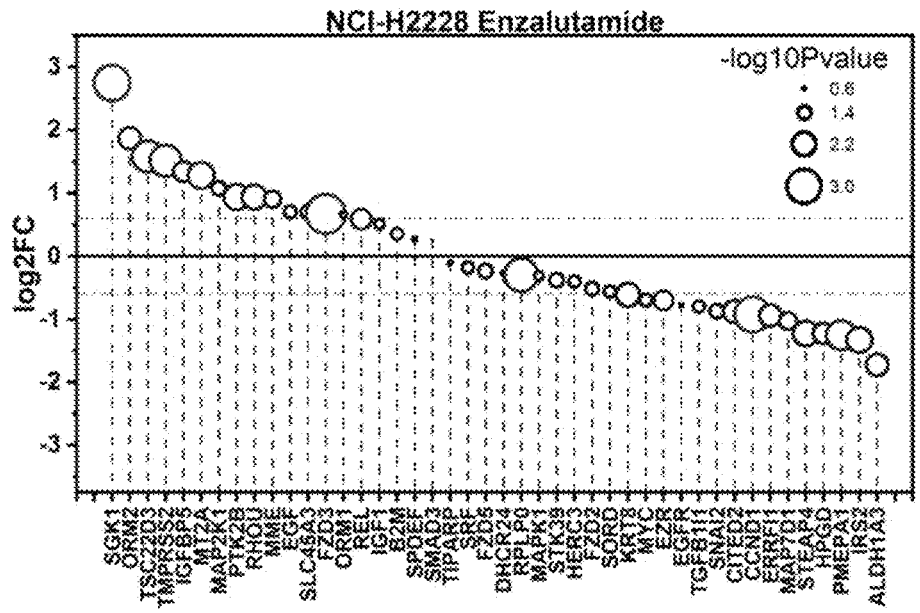
Figure 6D:
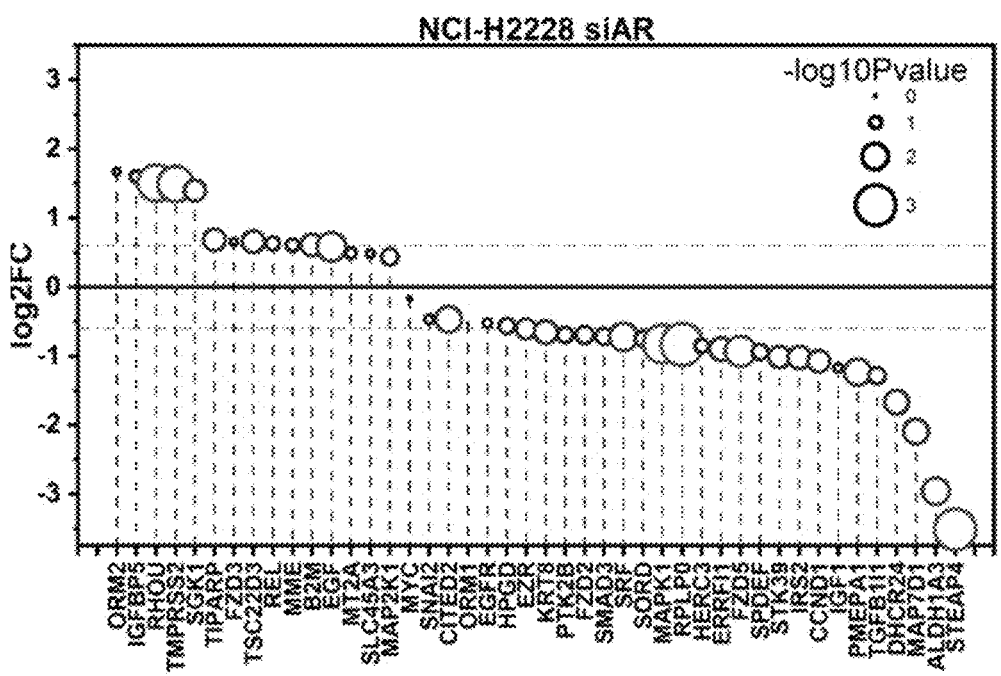

To understand how AR responds to its ligand and antagonist in lung cancer cell lines, the inventors measured changes in AR mRNA levels and protein translocation with qRT-PCR and immunofluorescent imaging, respectively. Liganded (R1881) AR in male A549 lung cancer cells was temporally downregulated (FIG. 1b), similar to what has been previously shown in prostate cancer cells2. In female H2228 lung cancer cells, AR expression exhibited minimal changes in response to androgen stimulation (FIG. 1b). Inhibition of AR with its antagonist enzalutamide, without ligand stimulation, resulted in increased AR expression in A549 and H2228 cells (FIG. 1c). AR stimulation with R1881 only downregulates AR expression in male A549 cells, but not in female H2228 cells, an effect that is blocked by pre-treatment with enzalutamide (FIG. 1c). This data establishes the ability of lung cells to regulate androgen mediated signaling. Growth inhibition of a panel of lung cancer cell lines treated with enzalutamide demonstrated half maximal effective concentration (EC50) similar to that of prostate cancer cells (range of 17-90 µM, FIG. 1d and Table 1) suggesting that AR signaling mediates pro-survival processes. Since AR is a transcription factor that can regulate several key target genes and modulate physiological processes like inflammation and pathological events such as cardiovascular disease and oncogenesis, translocation of AR to the nucleus could be a key determinant to set up a signaling platform for downstream effector genes. Liganded AR was efficiently transported to the nucleus in both A549 and H2228 cells (Red panel, FIGS. 1e and 1f, and FIGS. 4a and 4b), an effect that was disrupted using either enzalutamide or AR specific siRNA (FIGS. 1e and 1f, and FIG. 5).

TABLE 1

EC50 of lung cancer cell lines

| Cell Line | EC50 (µM) | |
|---|---|---|
| A549 | 39.890 | ±2.235 |
| NCI-H222B | 68.023 | ±2.982 |
| NCI-H226 | 60.362 | ±9.848 |
| NCI-H358 | 66.935 | ±1.714 |
| NCI-H460 | 68.682 | ±14.850 |
| NCI-H520 | 90.046 | ±9.291 |
| NCI-H1299 | 34.204 | ±1.610 |
| NCI-H1650 | 67.067 | ±4.370 |
| NCI-H1975 | 69.471 | ±3.620 |
| NCI-H3122 | 17.318 | ±1.349 |

Figure 1D:
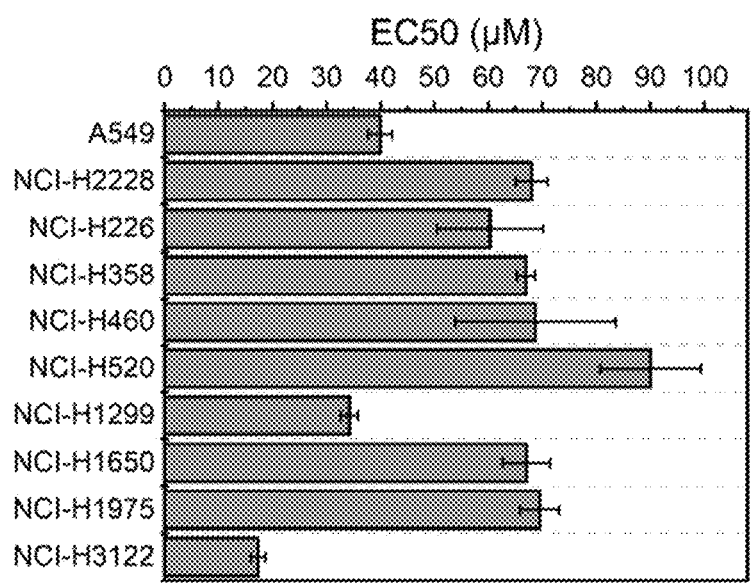
Figure 1E:
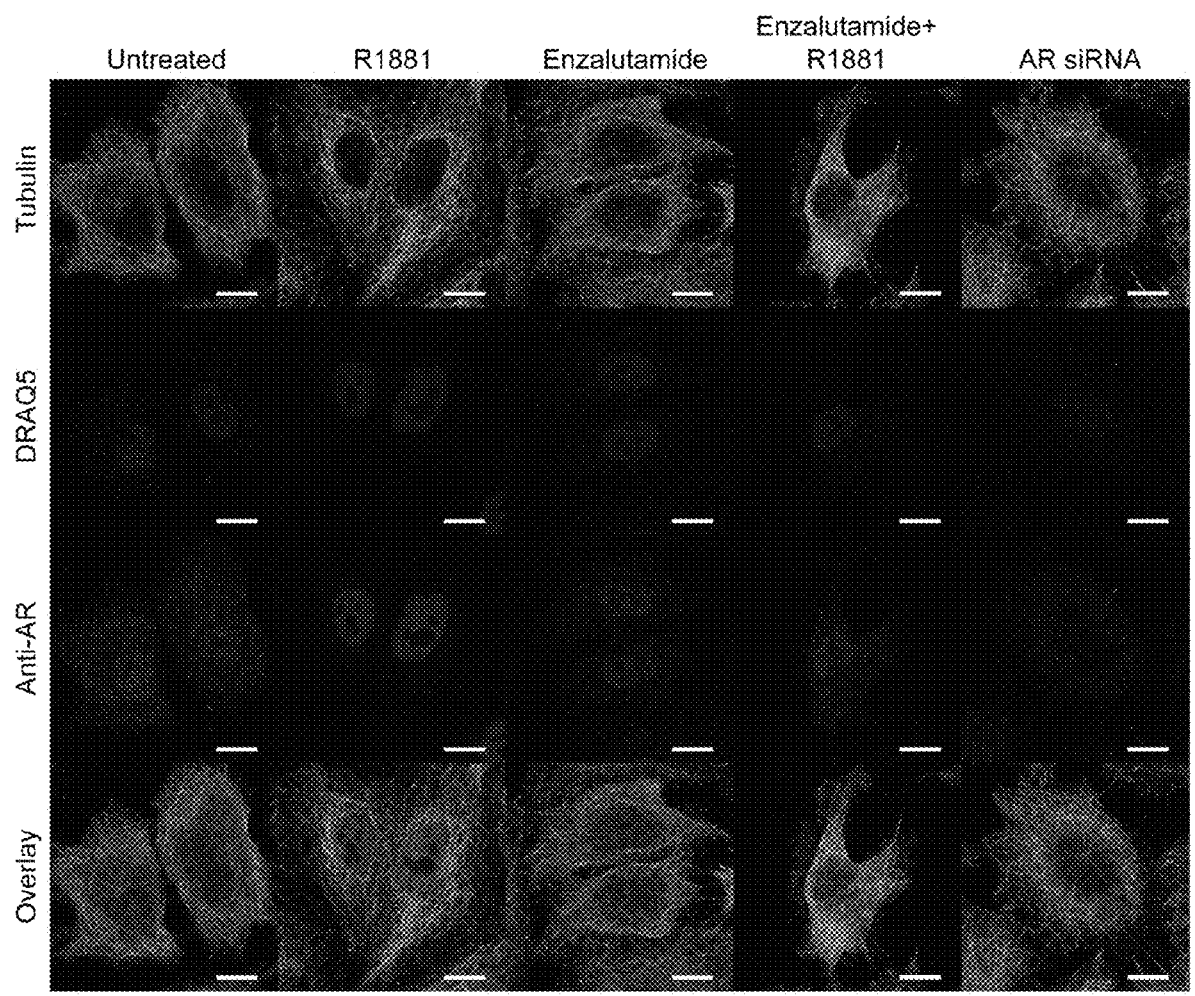
Figure 1F:
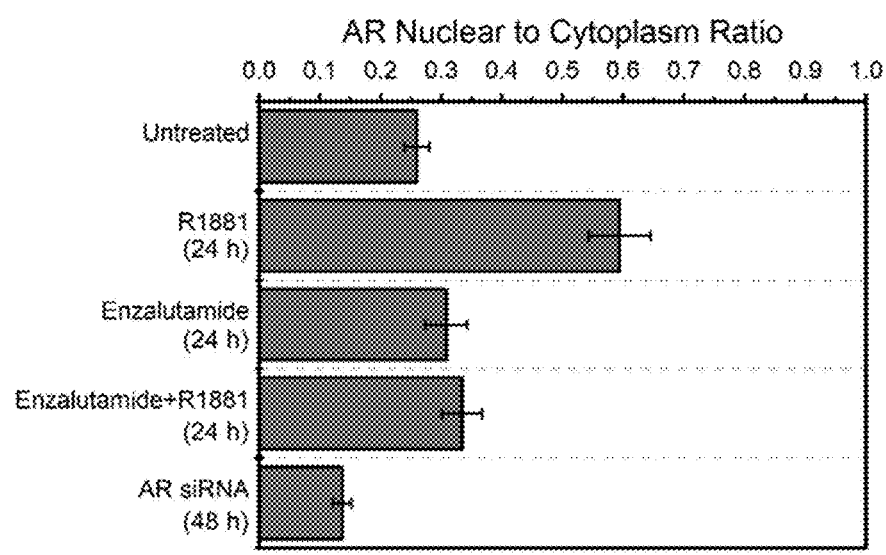

Half maximal effective concentration (EC50) of enzalutamide treatment on lung cancer cells at 72 h (FIG. 1d). The data are shown as EC50 ± SD.

Figure 2A:
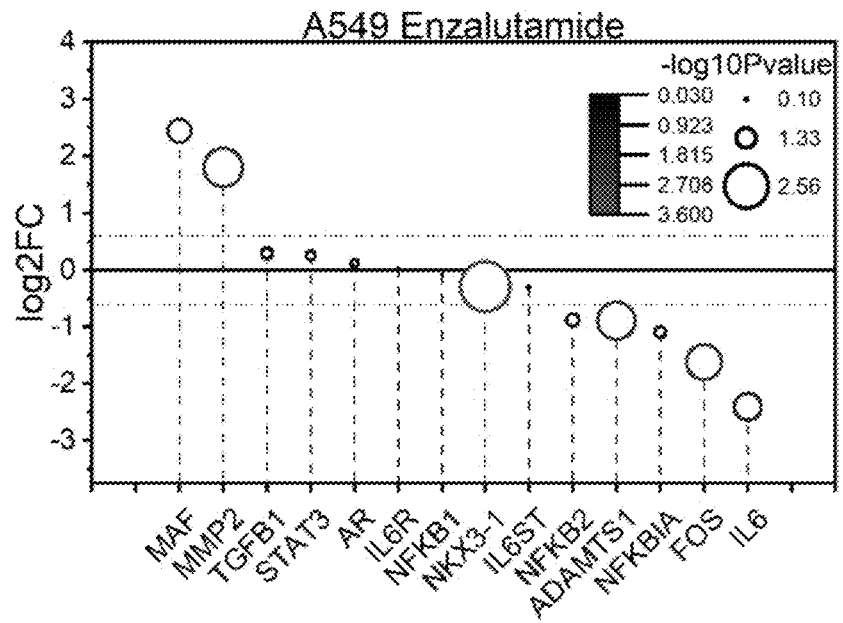
FIGS. 2A-2F shows enzalutamide and mRNA inhibition generates contrasting AR dependent signals in male and female lung cancer cells. 2A, Log 2 fold change (log 2FC) gene expressions of enzalutamide treated A549 were obtained from AR signaling panels. Genes with absolute values of log 2FC greater than 0.6 (represented by horizontal grey dash-dotted lines) and p-value less than 0.05 (or 1.3 in −log 10 scale) are considered significant. Circles with larger diameter and colored with red represent having more significant p-values. 2B, Log 2FC of A549 treated with AR siRNA. Blocking AR with enzalutamide and siRNA both resulted in downregulation of IL6 and FOS, as well as upregulation of MAF. 2C, 2D, Log 2FC of NCI-H2228 treated with enzalutamide and AR siRNA, respectively. In contrast to A549, IL6 was significantly upregulated in NCI-H2228. 2E, 2F, Respective DEGs of enzalutamide and AR siRNA treated A549 cells were used to construct separate gene interaction networks in iPathwayGuide1-4. Relationship between AR and IL6 is established through MAF, IL4, and IL13. Node color represents log 2FC (red: upregulation, blue: downregulation, grey: not measured), while the border of the node is darker as the p-value becomes more significant. Any isolated node was hidden in the final diagram.
Figure 2B:
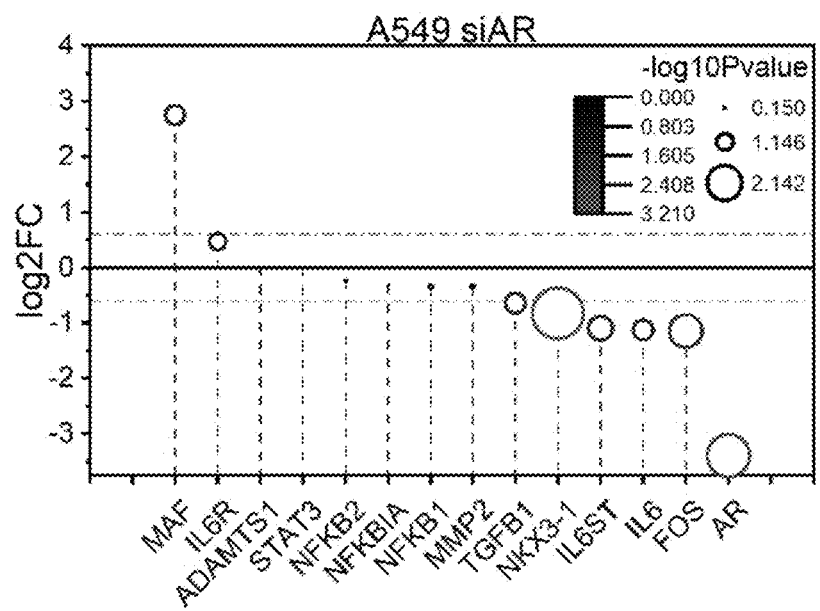
Figure 2C:
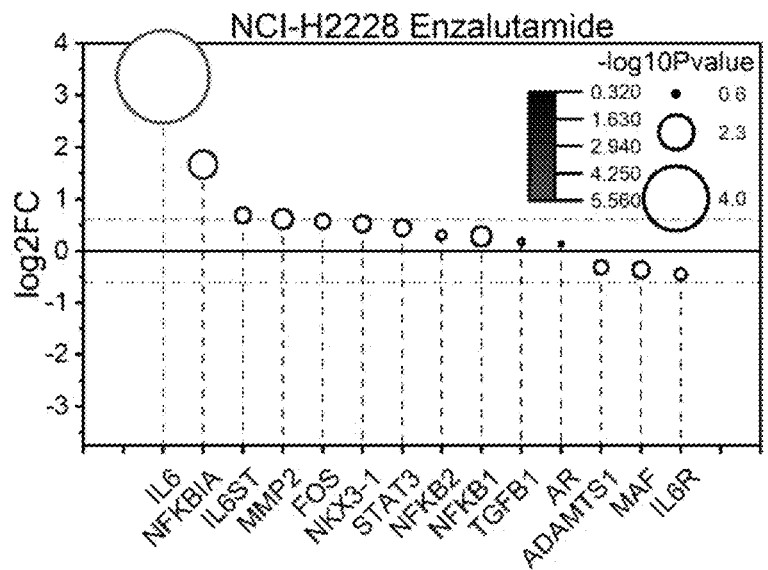
Figure 2D:
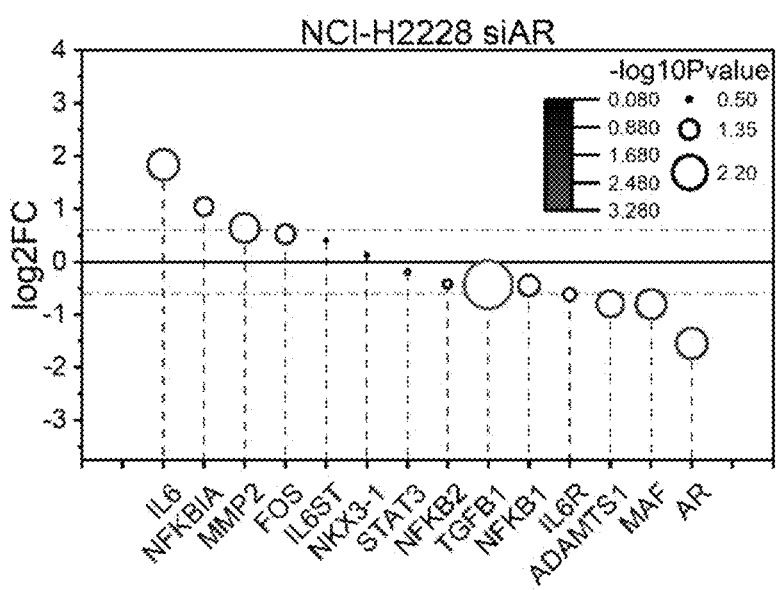

To understand how perturbing AR with enzalutamide or siRNA affects AR downstream signaling targets in A549 and H2228 cells, the inventors treated the cells with enzalutamide (5 µM) for 24 h or AR siRNA (10 nM) for 48 h, and the expression of AR responsive genes was measured using an AR signaling gene panel via qRT-PCR (Table 2 and FIG. 6). Out of the 115 genes measured, the inventors identified 12 and 11 genes to be significantly expressed in male A549 cells treated with enzalutamide and AR siRNA, respectively. Significant upregulation of MAF bZIP transcription factor (MAF) (log 2FC=2.44, p-value=0.035) and downregulation of IL6 (log 2FC=−2.41, p-value=0.023) and FOS (log 2FC=−1.627, p-value=0.008) were observed in A549 cells following enzalutamide treatment (FIG. 2a). Similarly, A549 cells with AR siRNA treatment also showed upregulation of MAF (log 2FC=2.75, p-value=0.056) and downregulation of IL6 (log 2FC=−1.13, p-value=0.0502) and FOS (log 2FC=−1.15, p-value=0.0102). In contrast, female H2228 cells demonstrated upregulation of IL6 and FOS, while the mRNA level of MAF was decreased following AR blockade (FIGS. 2c and 2d). The increased expression of IL6 in H2228 cells resembles one of the suggested androgen-independent disease progression mechanisms in prostate cancer. IL6 has been shown to cause androgen-independent activation of AR and induce some AR target genes such as prostate-specific antigen (PSA) through activation of signal transducer and activator of transcription 3 (STAT3), which directly interacts with the amino acids 234-558 of the AR N-terminal domain (NTD). In addition, another study also confirmed that enzalutamide treatment results in enhanced IL6 signaling cascade and increased STAT3 activation through upregulation of IL6ST and JAK1 expression in prostate cancer with enzalutamide resistance. Taken together with the lack of negative AR feedback loop in H2228 (FIG. 1b), the contrasting expression profiles of A549 and H2228 could potentially be attributed to androgen-independent pathways such as IL6 signaling.

TABLE 2

Complete AR signaling gene panel (Bio-Rad)
AR signaling gene panel

| ABCC4 | ELL2 | IRS2 | ORM2 | SOS1 |
|---|---|---|---|---|
| ABHD2 | ENDOD1 | JUN | PAK1IP1 | SP1 |
| ACSL3 | EP300 | KRT8 | PIAS1 | SFDEF |
| ACTB | ERRFI1 | LIFR | PIK3R3 | SRF |
| ADAMTS1 | EZR | LRIG1 | PMEPA1 | STAT3 |
| AKT1 | FAM105A | LRRFIP2 | PPAP2A | STEAP4 |
| ALDH1A3 | FKBP5 | MAF | PRKACB | STK39 |
| APPBP2 | FOS | MAP2K1 | PTK2B | TGFB1 |
| AR | FZD2 | MAP7D1 | RAB4A | TGFB1I1 |
| B2M | FZD3 | MAPK1 | RAF1 | TGFBR1 |
| CAMKK2 | FZD5 | MME | REL | TGFBR2 |
| CCND1 | GRB2 | MMP2 | RELA | TIPARP |
| CDKN1A | GSK3B | MT2A | RHOU | TMPRSS2 |
| CENPN | GUCY1A3 | MYC | RPLP0 | TPD52 |
| CITED2 | HERC3 | NCAPD3 | SEC22C | TRIB1 |
| CTNNB1 | HPGD | NCOA2 | SGK1 | TSC22D1 |
| CYP2U1 | HRAS | NCOR1 | SHC1 | TSC22D3 |
| DBI | IGF1 | NDRG1 | SLC26A2 | VAPA |
| DHCR24 | IGF1R | NFKB1 | SLC45A3 | VIPR1 |
| EAF2 | IGFBP5 | NFKB2 | SMAD3 | WIPI1 |
| EGF | IL6 | NFKBIA | SMS | WNT4 |
| EGFR | IL6R | NKX3-1 | SNAI2 | ZBTB10 |
| ELK1 | IL6ST | ORM1 | SORD | ZNF189 |

Full list of AR signaling genes measured in qRT-PCR (FIG. 2a-d and FIG. 6a-d). Genes are ordered alphabetically from top left to bottom right.

Figure 2E:
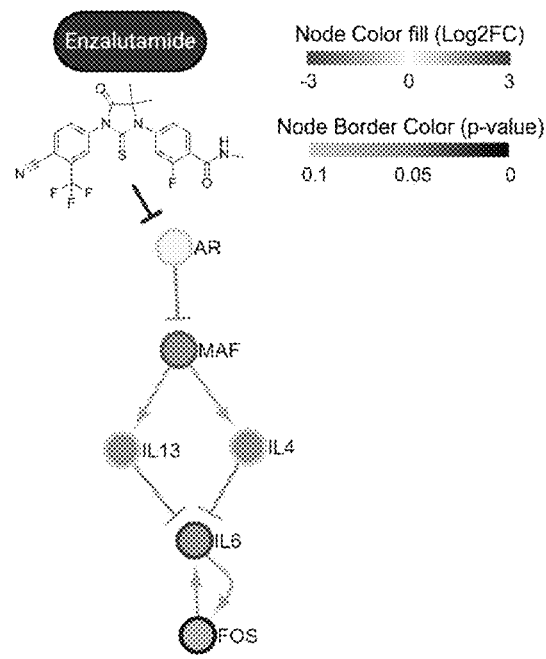
Figure 2F:
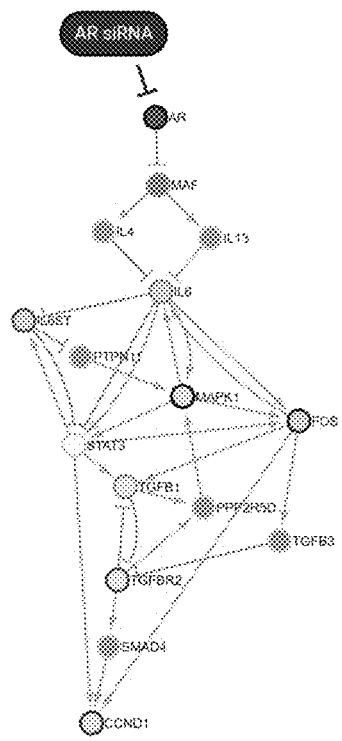

To further elucidate the interactions among the significantly expressed genes, the inventors reconstructed separate gene interaction networks in each treatment condition of A549 (FIGS. 2e and 2f). The resulting network indicates that by blocking AR signaling with enzalutamide, MAF upregulation may be due to the removal of AR inhibitory interaction on MAF which results in decreased expression of IL6 in part through IL13 and IL4 (FIG. 2e). This is consistent with a study in Th2 cells where it has been shown that MAF can promote expression of IL4 by binding directly to its promotor. AR signaling has also been shown to reduce IL4 production in the lung; and IL13, which shares many biological activities with IL4, has been observed to have anti-inflammatory effects in vitro and in vivo by inhibiting production of proinflammatory cytokines and chemokines. Taken together, the network analysis and these previous studies suggest that IL4 and IL13 have inhibitory effects on IL6 resulting in suppression of IL6 expression (FIG. 2e). This relationship is further validated by AR inhibition with siRNA, which also induces MAF upregulation and IL6 downregulation (FIG. 2f).

IL6 signaling occurs through two main pathways denoted as cis-signaling and trans-signaling. IL6 trans-signaling in particular occurs on potentially all cell surfaces including lung epithelial, endothelial, and smooth muscle cells and has been linked to inflammatory diseases of the lung including asthma and the acute inflammatory response to viral infections. IL6 pathway activates the Janus kinase signal transducer and activator of transcription (JAK/STAT) signaling axis and contribute to cytokine release syndrome. Since IL6 has prominent proinflammatory properties and plays a dominate role in the cytokine release syndrome seen in COVID-19 patients, it has been proposed to be a predictive marker of impending respiratory failure and efforts are now underway investigating agents that inhibit the IL6 pathway to dampen the cytokine storm seen in COVID-19.

Figure 3A:
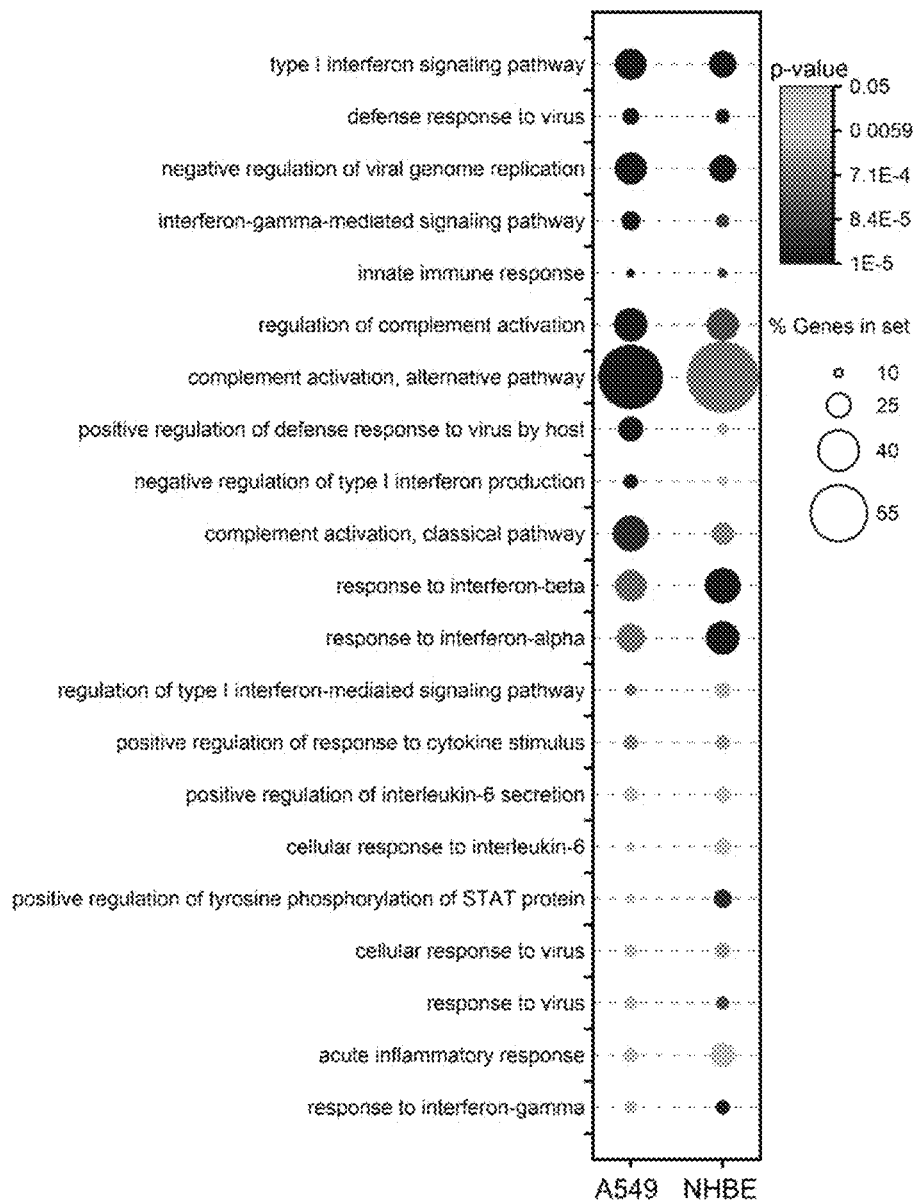
FIGS. 3A-3E shows RNA-seq of SARS-CoV-2 infected A549 and normal human bronchial epithelial (NHBE) cells suggests an AR/MAF driven mechanism that regulates IL6 and its downstream inflammatory genes. 3A, Selective inflammatory and immune related GO Biological Process terms that are significantly enriched for differentially expressed genes (DEGs) in both SARS-CoV-2 infected A549 and NHBE cells. The color of the circles represents pvalue significance, while the size corresponds to the percentage of DEGs in the total gene set. The order of GO terms is ranked by the p-values obtained from A549 cells. 3B, Inflammatory response (M5932) was one of the top significant gene sets when GSEA analysis was performed on MSigDB's Hallmark gene sets (H collection, v7.1). 3C, Inflammatory gene expressions of SARS-CoV-2 infected A549 and NHBE. All genes are differentially expressed for NHBE, while the DEGs for A549 are marked with asterisks (adjusted pvalue: P<0.01, *P<0.001). Colors represent z-scores of the normalized read counts across all samples within individual cell lines. 3D, Comparison of gene expressions obtained from enzalutamide, AR siRNA, and SARS-CoV-2 treated lung cells. 3E, DEGs of NHBE in the JAK-STAT signaling pathway (based on KEGG pathway database) and a custom gene list (see methods for more details) was used to create gene interaction networks in iPathwayGuide. Gene expressions of A549 and NHBE were plotted side by side (left circle: NHBE, right circle: A549) for comparison. Compared to AR inhibition in A549, SARS-CoV-2 infection causes opposite gene expressions of IL6 and MAF in NHBE/A549.
Figure 3B:
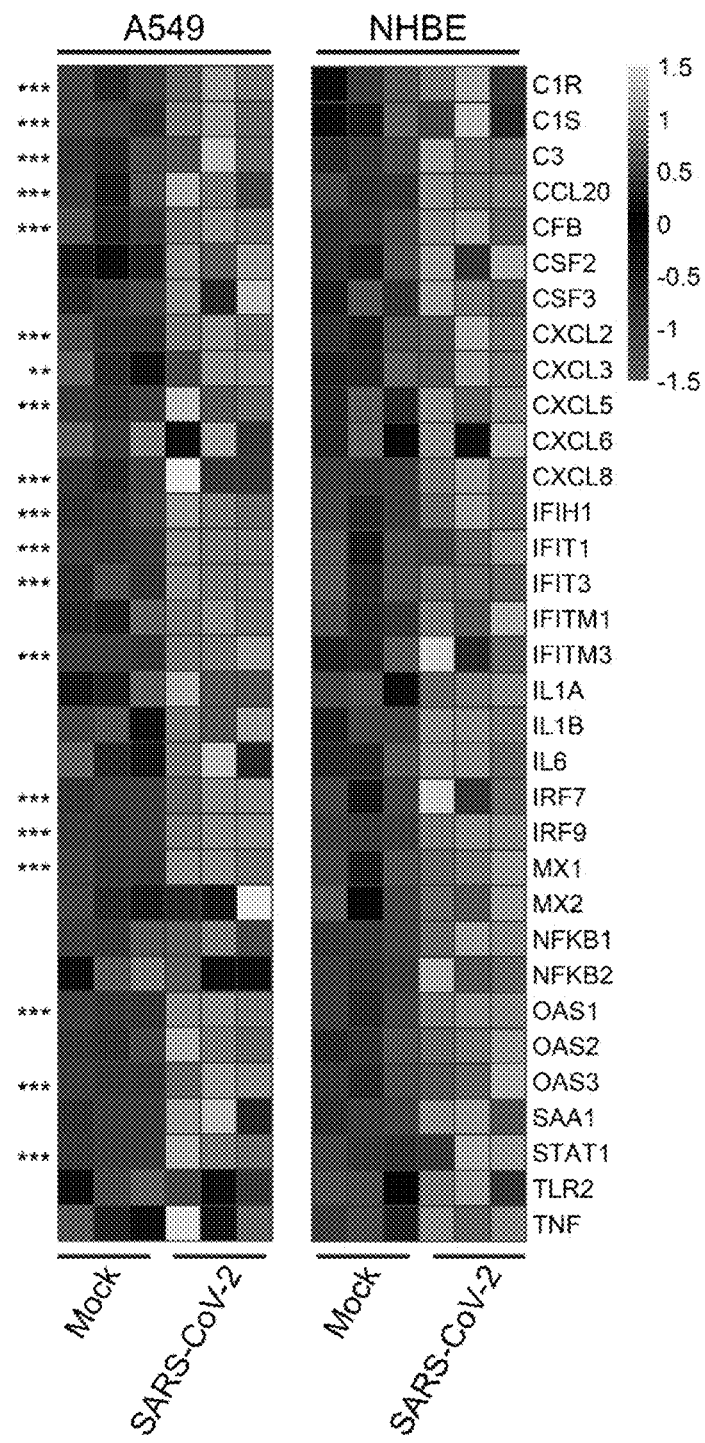
Figure 3C:
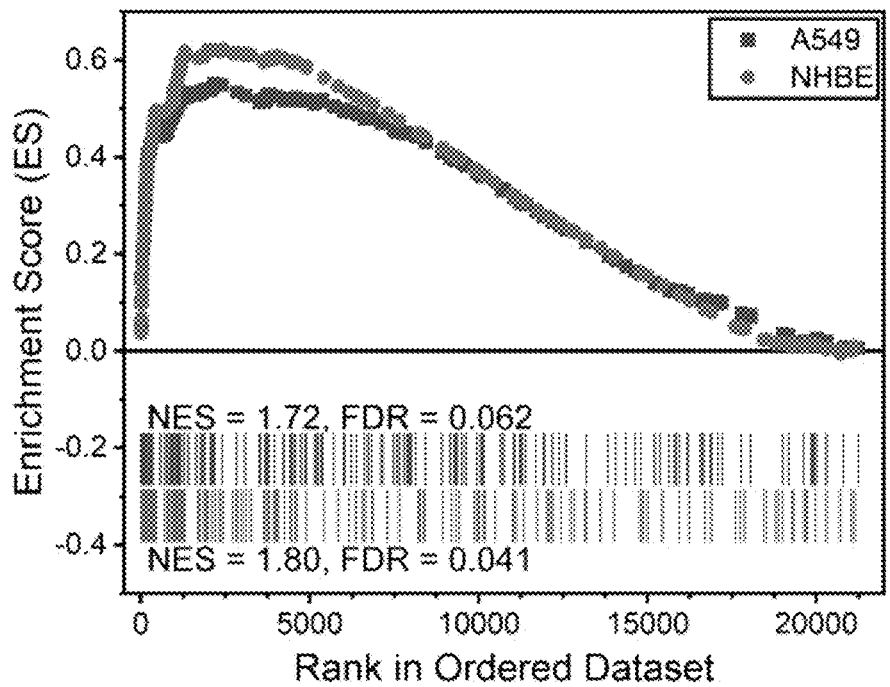

To provide evidence that the anti-androgen enzalutamide can potentially decrease IL6 production in lung cells in the setting of COVID-19, the inventors re-analyzed the RNA sequencing (RNA-seq) data from Blanco-Melo et al. 2020, where they investigated both A549 and normal human bronchial epithelial (NHBE) cells infected with SARS-CoV-2. Gene Ontology (GO) analysis revealed many inflammatory and immune-related GO terms to be significant in both A549 and NHBE cells. Shared GO terms such as several interferon signaling pathways, defense response to virus, complement activation, regulation of IL6 and STAT proteins were highly significant (FIG. 3a and Table 3). The interferon (IFN)-mediated immune response is engaged after detection of invading pathogens such as RNA and DNA viruses. IFN pathway related genes including interferon induced transmembrane protein 3 (IFITM3), IFN-regulatory factor 7 and 9 (IRF7 and IRF9), STAT1, and MX dynamin like GTPase 1 (MX1) are all significantly upregulated in both A549 and NHBE following SARS-CoV-2 infection (FIG. 3b). Both A549 and NHBE cells also expressed elevated levels of several complement components from the classical (C1S and C1R) and alternative (CFB) pathways (FIG. 3b). Complement C3, which can be cleaved into C3a and C3b, can act as a co-stimulator that can increase IL6 expression in lipopolysaccharide signaling, and help the formation of C5 convertase, which can induce expressions of tumor necrosis factor (TNF) and IL1β in monocytes and macrophages. Gene set enrichment analysis (GSEA) was performed with the Hallmark gene set collection (v7.1) from the Molecular Signatures Database (MSigDB) to survey for enriched hallmark biological processes within the SARS-CoV-2 infected cells. Inflammatory response is one of the top enriched gene sets found in both A549 and NHBE (FIG. 3c). The core enriched genes that contribute the most to the enrichment results include interleukins (IL1A, IL1B, IL6, IL7R), chemokines (CCL20, CXCL6, CXCL8, CXCL10), and interferon genes (IRF7, IFITM1). Other hallmark gene sets such as IL6-JAK-STAT3 signaling, complement, TNFA signaling via NFKB, and interferon responses are also highly enriched in both cell lines (Table 4). Taken together, SARS-CoV-2 infection results in significant increases of inflammatory genes that are involved in IL6 and interferon signaling. Similar gene expression patterns and enrichment results can be observed in both A549 and NHBE (FIG. 3a, 3b and Table 4), suggesting similar viral responses to SARS-CoV-2.

TABLE 3

Selective inflammatory and immune related GO Biological Process terms

| | | A549 | | | | NHBE | | | |
|---|---|---|---|---|---|---|---|---|---|
| | GO ID | Count DEG | Count All | % gene | p-value (Elim) | Count DEG | Count All | % gene | p-value (Elim) |
| type I interferon signalling pathway | GO:0060337 | 16 | 61 | 29.5 | 5.70E−24 | 18 | 72 | 25.0 | 8.70E−15 |
| defense reponse to virus | GO:0051607 | 24 | 151 | 15.9 | 2.60E−17 | 23 | 172 | 13.4 | 8.30E−11 |
| negative regulation of viral genome replication | GO:0045067 | 12 | 640 | 30.0 | 7.00E−17 | 12 | 47 | 25.5 | 1.30E−11 |
| interferon-gamma-mediated signaling pathway | GO:0060333 | 10 | 56 | 17.9 | 1.80E−09 | 8 | 64 | 12 5 | 1.10E−04 |
| innate immune response | GO:0045067 | 41 | 483 | 8.5 | 6.00E−06 | 51 | 560 | 9.1 | 5.60E−06 |
| regulation of complement activation | GO:0030449 | 5 | 16 | 31.3 | 3.70E−06 | 6 | 20 | 30.0 | 1.60E−04 |
| complement activation, alternative pathway | GO:0006957 | 3 | 5 | 60.0 | 4.20E−06 | 2 | 3 | 66.7 | 8.60E−04 |
| positive regulation of defense response to virus by host | GO:0002230 | 4 | 17 | 23.5 | 6.80E−06 | 2 | 18 | 11.1 | 3.70E−02 |
| negative regulation of type I interferon production | GO:0032480 | 5 | 36 | 13.9 | 6.90E−06 | 4 | 39 | 10.3 | 4.23E−03 |
| complement activation, classical pathway | GO:0006958 | 3 | 9 | 33.3 | 3.40E−06 | 3 | 14 | 21.4 | 1.55E−03 |
| response to interferon-beta | GO:0035456 | 5 | 17 | 29.4 | 5.20E−04 | 7 | 21 | 33.3 | 3.60E−08 |
| response to interferon-alpha | GO:0035455 | 4 | 15 | 26.7 | 7.90E−04 | 6 | 19 | 31.6 | 5.10E−07 |
| regulation of type I interferon-mediated signaling pathway | GO:0060338 | 3 | 26 | 11.5 | 9.60E−04 | 4 | 27 | 14.8 | 3.27E−02 |
| positive regulation of response to cytokine stimulus | GO:0060760 | 5 | 36 | 13.9 | 1.65E−03 | 6 | 43 | 14.0 | 2.20E−03 |
| positive regulation of interleukin-6 secretion | GO:2000778 | 2 | 14 | 14.3 | 4.88E−03 | 3 | 20 | 15.0 | 4.50E−03 |
| cellular response to interleukin-6 secretion | GO:0071354 | 2 | 22 | 9.1 | 1.19E−02 | 4 | 25 | 16.0 | 1.17E−02 |
| positive regulation of tyrosine phosphorylation of STAT protein | GO:0042531 | 2 | 22 | 9.1 | 1.19E−02 | 6 | 35 | 17.1 | 2.40E−06 |
| cellular response to virus | GO:0098586 | 5 | 39 | 12.8 | 176E−02 | 6 | 42 | 14.3 | 2.20E−03 |
| response to virus | GO:0009615 | 26 | 210 | 12.4 | 2.44E−02 | 30 | 239 | 12.6 | 1.40E−04 |
| acute inflammatory response | GO:0002526 | 8 | 58 | 13.5 | 3.04E−02 | 17 | 72 | 23.6 | 5 49E−03 |
| response to interferon-gamma | GO:0034341 | 12 | 106 | 11.3 | 4.33E−02 | 17 | 128 | 13.3 | 2.70E−06 |

The GO terms were ordered by the p-vaules obtained form A459 cells. The number of differentially expressed genes (Count DEG) was shown with the total number of measured genes (Count All). The % gene was calculated by (Count DEG)/(Count All). Elim method was used to correct p-values.

TABLE 4

Top 20 enriched Hallmark gene sets for A549 and NHBE in SGEA

| NAME | SIZE | ES | NES | FDR |
|---|---|---|---|---|
| A549 | | | | |
| Complement | 166 | 0.489 | 1.766 | 0.081 |
| Inflammatory Response | 154 | 0.552 | 1.715 | 0.062 |
| TNFA Signaling via NFKB | 191 | 0.496 | 1.710 | 0.055 |
| Coagulation | 108 | 0.426 | 1.669 | 0.106 |
| IL6 JAK STAT3 Signaling | 71 | 0.529 | 1.657 | 0.145 |
| Interferon Gamma Response | 177 | 0.800 | 1.653 | 0.128 |
| Allograft Rejection | 135 | 0.500 | 1.636 | 0.121 |
| Unfolded Protein Responsre | 113 | 0.374 | 1.603 | 0.119 |
| KRAS Signaling Up | 152 | 0.446 | 1.533 | 0.135 |
| Interferon Alpha Response | 95 | 0.868 | 1 476 | 0.132 |
| Apoptosis | 142 | 0.316 | 1.467 | 0.132 |
| MYC Targets VI | 200 | 0.453 | 1.450 | 0.138 |
| Angiogenesis | 31 | 0.421 | 1.449 | 0.131 |
| Glycolysis | 186 | 0.290 | 1.441 | 0.132 |
| DNA Repair | 150 | 0.246 | 1 436 | 0.126 |
| UV Response Up | 149 | 0.259 | 1.416 | 0.133 |
| Hypoxia | 185 | 0.235 | 1.413 | 0.128 |
| Epithelial Mesechymal Transition | 176 | 0.303 | 1.410 | 0.130 |
| IL2 STAT5 Signaling | 172 | 0.300 | 1.382 | 0.146 |
| Fatty Add Metabolism | 141 | 0.306 | 1.354 | 0.175 |
| NHBE | | | | |
| KRAS Signaling Up | 162 | 0.553 | 2.178 | 0.041 |
| Apoptosis | 153 | 0.452 | 1.965 | 0.041 |
| IL6 JAK STAT3 Signaling | 68 | 0.677 | 1.886 | 0.041 |
| Complement | 173 | 0.533 | 1.828 | 0.041 |
| Interferon Gamma Response | 183 | 0.656 | 1.612 | 0.041 |
| Allograft Rejection | 145 | 0.454 | 1.809 | 0.041 |
| TNFA Signaling Via NFKB | 194 | 0.718 | 1.806 | 0.041 |
| Inflammatory Response | 159 | 0.622 | 1.602 | 0.041 |
| MYC Targets V2 | 58 | 0.550 | 1.734 | 0.041 |
| Hypoxia | 187 | 0.379 | 1.716 | 0.041 |
| Unfolded Protein Response | 112 | 0.421 | 1.690 | 0.052 |
| UV Response Up | 143 | 0.440 | 1.687 | 0.051 |
| Interferon Alpha Response | 97 | 0.721 | 1.683 | 0.050 |
| IL2 STAT5 Signaling | 172 | 0.376 | 1.653 | 0.053 |
| Reactive Oxygen Spedes Pathway | 48 | 0.371 | 1.585 | 0.069 |
| Coagulation | 114 | 0.444 | 1.553 | 0.070 |
| mTORC1 Signaling | 198 | 0.284 | 1.549 | 0.071 |
| Cholesterol Homeostasis | 70 | 0.301 | 1.543 | 0.070 |
| Xenobiotic Metabolism | 166 | 0.333 | 1.459 | 0.117 |
| Epthelial Mesechymal Transition | 191 | 0.395 | 1 440 | 0.129 |

Figure 3D:
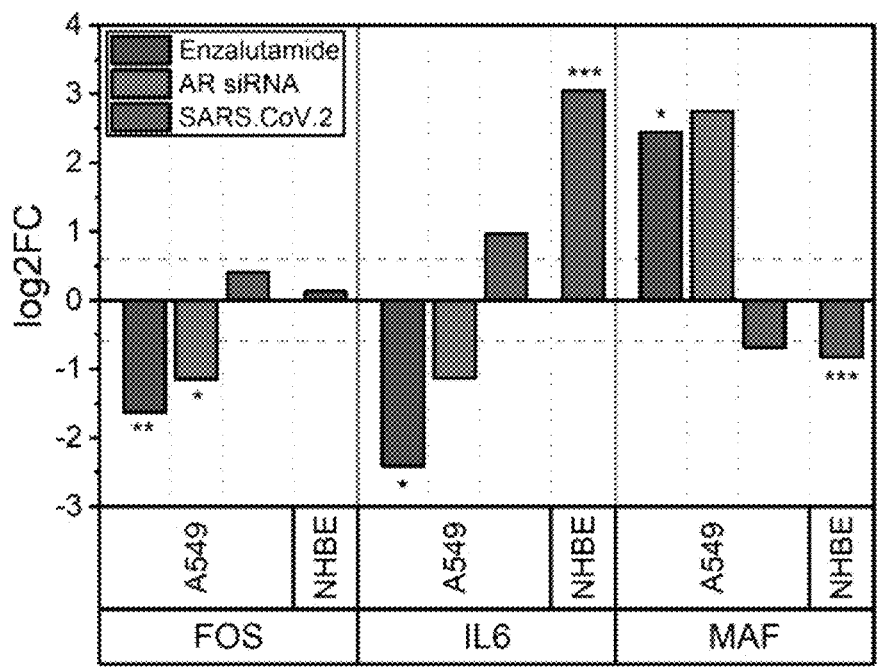
Figure 3E:
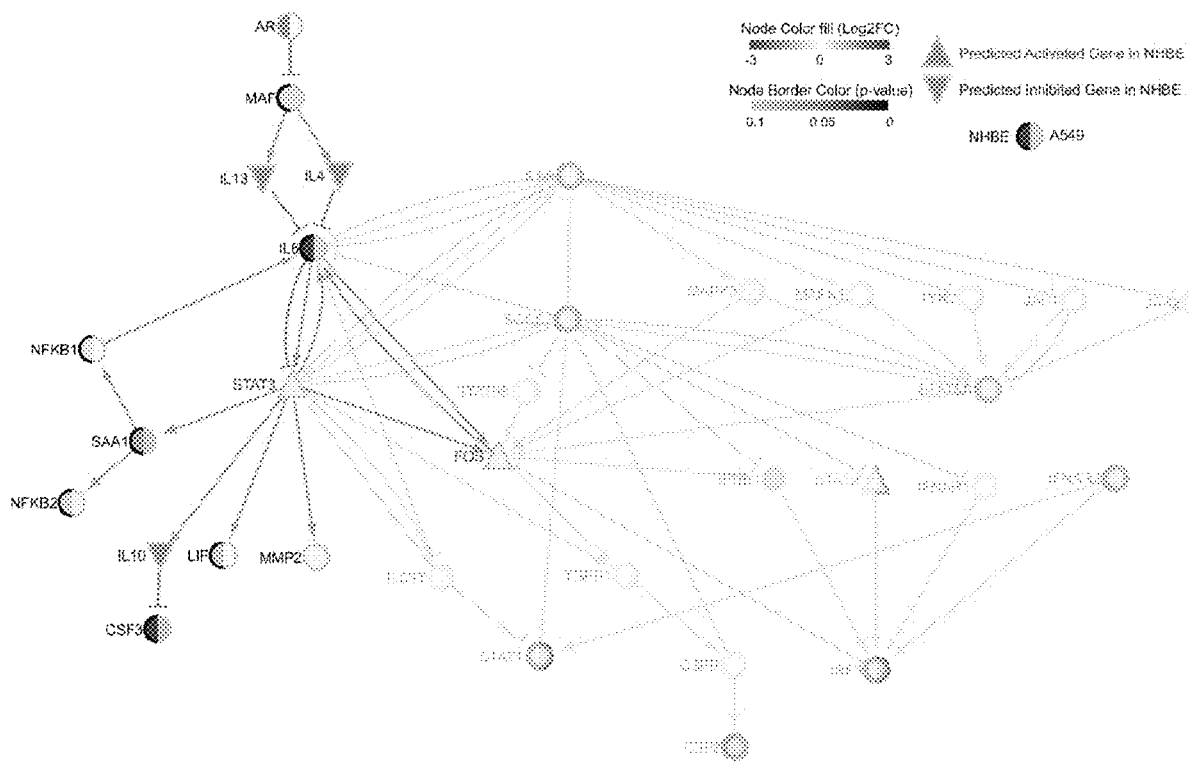
Figure 4A:
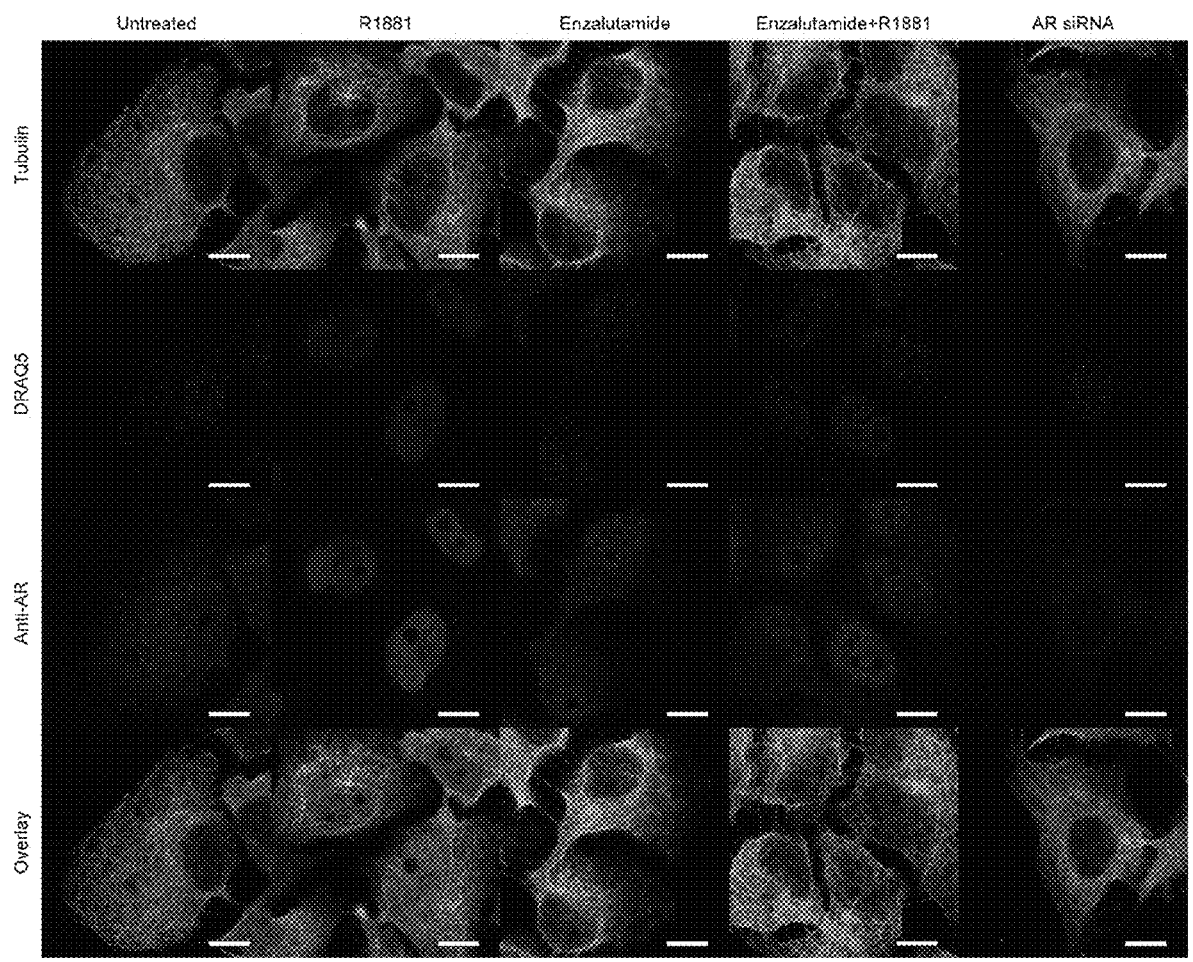
FIGS. 4A-4B shows AR immunofluorescent images for NCI-H2228 cells, related to FIGS. 1E-1F. 4A, Representative immunofluorescent images of AR proteins in H2228 treated with 1 nM R1881, 5 µM Enzalutamide (with or without 1 nM R1881), or AR siRNA (scale bar: 10 µm). 4B, Ratio of quantified AR immunofluorescent signals within the nucleus to the entire cell region (H2228). Data are presented as Mean±SD.
Figure 4B:
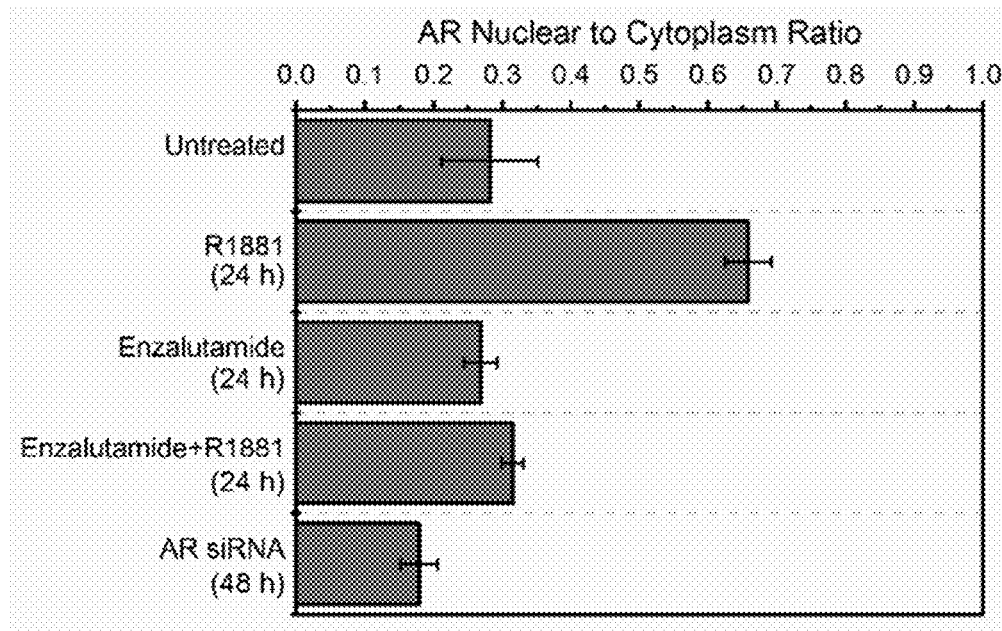
Figure 7A:
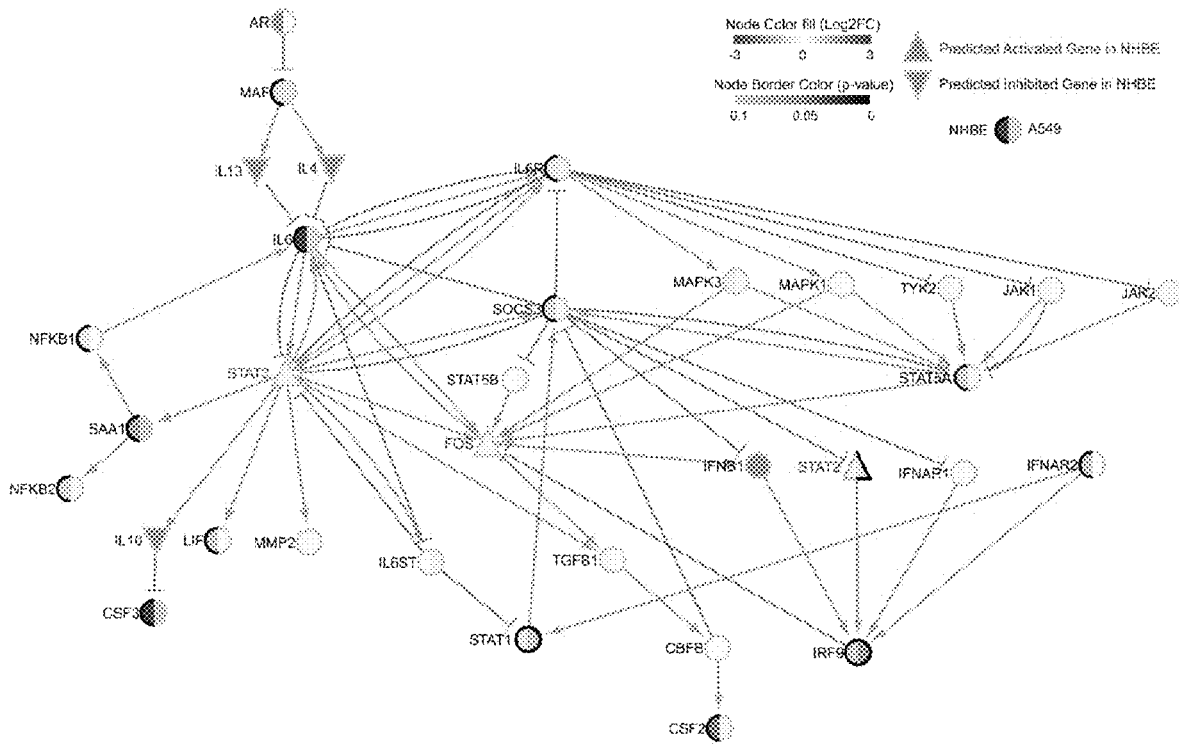
FIGS. 7A-7B shows full network analysis for NHBE and A549 cells, related to FIG. 3E. 7A, DEGs of NHBE in the JAK-STAT signaling pathway (based on KEGG pathway database) and a custom gene list (see methods for more details) was used to create gene interaction networks in iPathwayGuide. Gene expressions of A549 and NHBE were plotted side by side (left half circle: NHBE, right half circle: A549) for comparison. This is the full version of FIG. 3E. 7B, The degree centrality (y-axis), closeness centrality (circle size), and betweenness centrality (color scale) of each gene in the network are shown here.
Figure 7B:
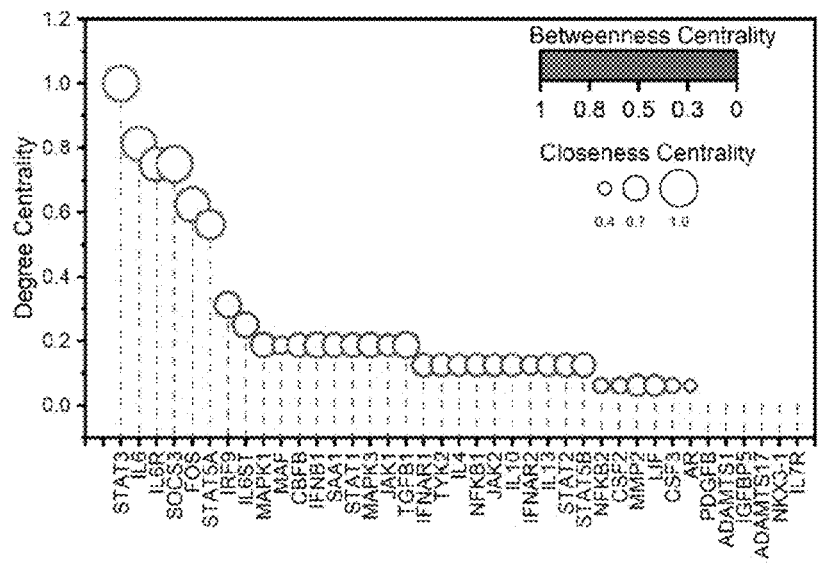

Top 20 GSEA Hallmark gene sets for A549 (left) and NHBE (right) RNA sequencing data. The size of the gene set, enrichment score (ES), normalized enrichment score (NES), and false discovery rate (FDR) are shown. The gene sets are ordered based on NES of individual cells By inhibiting AR, IL6 and MAF show contrasting expression in A549 cells (FIGS. 2a and 2b; FIG. 3d). More specifically, IL6 is upregulated in A549 and NHBE cells when infected with SARS-CoV-2, but it is downregulated with treatment of enzalutamide or AR siRNA. The expression of MAF is decreased with SARS-CoV-2 infection, but it is increased with AR blockade. Since both IL6 and interferon signaling initiate the JAK-STAT pathway, the inventors explored the potential of using AR inhibition in COVID-19 patients by reconstructing a regulatory network using the differentially expressed genes (DEGs) of NHBE in the JAK-STAT pathway and other genes of interest based on the AR data (FIGS. 2a and 2b). The DEGs of NHBE were used instead of A549 because even though many gene expressions of A549 show similar trends as NHBE, A549 is less permissive to SARS-CoV-2 due to low expression of the viral receptor angiotensin-converting enzyme 2 (ACE2). Network analysis on the RNA-seq data of NHBE cells infected with SARS-CoV-2 reveals the same regulatory interactions between AR and IL6 (FIG. 3e, FIG. 7, and Table 5) as those present in the AR data treated with enzalutamide or AR siRNA (FIGS. 2e and 2f). In contrast to the gene expression data from A549 following AR inhibition, SARS-CoV-2 infection induced significant downregulation of MAF and upregulation of IL6 in NHBE. Moreover, upstream regulator analysis predicted IL4 and IL13 were both inhibited in NHBE (Table 6), aligning with the network diagram (FIG. 3e) which indicates that lower expression of MAF regulated IL4 and IL13 can be one of the mechanisms that leads to increased IL6 expression in SARS-CoV-2 infected cells. While IL6 and MAF expression in A549 cells with SARS-CoV-2 infection did not have significant p-values (0.077 and 0.31, respectively), their log 2FCs indicate that IL6 was upregulated (0.968) and MAF was downregulated (−0.68). STAT3 is also predicted to be activated using upstream regulator analysis (Table 6). STAT3 can activate serum amyloid A1 (SAA1), a protein involved in inflammation and produced in acute injury. SAA1 has been shown to induce transcriptional activities of inflammatory genes such as nuclear factor kappa B in myocytes and lung cells via Toll-like receptors. NFKB1 activates IL6, thus forming a positive feedback loop between IL6, STAT3, SAA1, and NFKB1. IL6 and STAT3 are the top two nodes in terms of degree centrality and betweenness centrality, indicating that they are the most connected nodes and the crucial gatekeepers in this network, which contains many genes related to inflammatory response and/or from the JAK-STAT pathway. With the predicted regulatory connections from AR to IL6 through MAF and IL4/IL13 as suggested by the network analysis in data from both AR perturbation experiments as well as data from COVID-19 patients, the inventors propose that AR inhibition through enzalutamide may be a useful approach to dampen the inflammatory response caused by IL6 in COVID-19 patients.

TABLE 5

Results of network analysis for A549 and NHBE

| Genes | | Centrality | | | A549 | | | NHBE | | |
|---|---|---|---|---|---|---|---|---|---|---|
| name | entrez | Degree | Closeness | Betweenness | log2FC | p-value | adj pu | log2FC | p-value | adj pu |
| STAT3 | 6774 | 1 | 1 | 1 | 0.04 | 6.42E−01 | 8.92E−01 | 0.19 | 3.30E−02 | 3.37E−01 |
| IL6 | 3569 | 0.813 | 0.947 | 0.929 | 0.97 | 7.69E−02 | NA | 3.05 | 2.17E−23 | 7.96E−21 |
| IL6R | 3570 | 0.750 | 0.926 | 0.381 | −0.28 | 1.28E−01 | 5.42E−01 | −0.58 | 1.17E−05 | 8.54E−04 |
| SOCS3 | 9021 | 0.750 | 1 | 0.810 | 0.22 | 1.23E−01 | 5.35E−01 | 1.04 | 2.74E−07 | 2.76E−05 |
| FOS | 2353 | 0.625 | 0.959 | 0.421 | 0.41 | 1.63E−01 | 5.89E−01 | 0.13 | 1.95E−01 | 6.89E−01 |

TABLE 5-continued

Results of network analysis for A549 and NHBE

| Genes | | Centrality | | | A549 | | | NHBE | | |
| --- | --- | --- | --- | --- | --- | --- | --- | --- | --- | --- |
| name | entrez | Degree | Closeness | Betweenness | log2FC | p-value | adj pu | log2FC | p-value | adj pu |
| STAT5A | 6776 | 0.563 | 0.829 | 0.166 | −0.16 | 3.79E−01 | 7.53E−01 | 1.18 | 2.77E−04 | 1.23E−02 |
| IRF9 | 10379 | 0.313 | 0.742 | 0.089 | 2.43 | 1.12E−88 | 2.74E−85 | 1.29 | 5.65E−29 | 2.69E−26 |
| IL6ST | 3572 | 0.250 | 0.716 | 0.054 | 0.29 | 2.16E−01 | 6.42E−01 | −0.02 | 8.95E−01 | 9.82E−01 |
| CBFB | 865 | 0.188 | 0.689 | 0.179 | 0.01 | 9.70E−01 | 9.93E−01 | 0.01 | 9.17E−01 | 9.87E−01 |
| IFNB1 | 3456 | 0.188 | 0.714 | 0.006 | NA | NA | NA | NA | NA | NA |
| JAK1 | 3716 | 0.188 | 0.631 | 0.001 | 0.04 | 5.70E−01 | 8.61E−01 | 0.15 | 1.10E−01 | 5.64E−01 |
| MAF | 4094 | 0.188 | 0.533 | 0.216 | −0.68 | 3.11E−01 | NA | −0.83 | 9.05E−09 | 1.20E−06 |
| MAPK1 | 5594 | 0.188 | 0.693 | 0.003 | 0.03 | 7.32E−01 | 9.21E−01 | −0.05 | 5.70E−01 | 9.04E−01 |
| MAPK3 | 5595 | 0.188 | 0.693 | 0.003 | 0.11 | 2.95E−01 | 7.03E−01 | 0.41 | 8.05E−03 | 1.44E−61 |
| SAA1 | 6288 | 0.188 | 0.681 | 0.171 | 1.24 | 1.85E−02 | NA | 2.20 | 2.08E−70 | 5.95E−67 |
| STAT1 | 6772 | 0.188 | 0.689 | 0.110 | 1.32 | 2.21E−51 | 2.71E−48 | 0.54 | 2.39E−08 | 2.97E−06 |
| TGFB1 | 7040 | 0.188 | 0.738 | 0.053 | 0.02 | 8.35E−01 | 9.54E−01 | 0.17 | 1.15E−01 | 5.73E−01 |
| IFHAR1 | 3454 | 0.125 | 0.684 | 0.005 | 0.03 | 8.24E−01 | 9.51E−01 | 0.08 | 4.82E−01 | 8.70E−01 |
| IFNAR2 | 3455 | 0.125 | 0.569 | 0.007 | −0.01 | 9.51E−01 | 9.87E−01 | 1.38 | 3.10E−05 | 1.92E−03 |
| IL10 | 3586 | 0.125 | 0.648 | 0.146 | NA | NA | NA | NA | NA | NA |
| IL13 | 3596 | 0.125 | 0.642 | 0.136 | NA | NA | NA | NA | NA | NA |
| IL4 | 3565 | 0.125 | 0.642 | 0.136 | NA | NA | NA | NA | NA | NA |
| JAK2 | 3717 | 0.125 | 0.631 | 0.001 | 0.24 | 2.60E−01 | 6.94E−01 | 0.15 | 4.28E−01 | 8.49E−01 |
| NFKB1 | 4790 | 0.125 | 0.642 | 0.023 | 0.00 | 9.75E−01 | 9.93E−01 | 0.54 | 8.86E−06 | 9.67E−06 |
| STAT2 | 6773 | 0.125 | 0.664 | 0.005 | 0.59 | 3.59E−03 | 6.76E−06 | 0.28 | 3.36E−03 | 8.23E−02 |
| STAT5B | 6777 | 0.125 | 0.681 | 0.002 | −0.08 | 4.09E−01 | 7.73E−01 | 0.01 | 9.55E−01 | 9.93E−01 |
| TYK2 | 7297 | 0.125 | 0.631 | 0.001 | −0.09 | 4.09E−01 | 7.73E−01 | 0.20 | 1.42E−01 | 6.16E−01 |
| AR | 367 | 0.063 | 0.4 | 0 | −0.04 | 7.05E−01 | 9.13E−01 | −0.87 | 4.98E−01 | NA |
| CSF2 | 1437 | 0.063 | 0.486 | 0 | 0.17 | 7.19E−01 | NA | 2.93 | 6.93E−10 | 1.12E−07 |
| CSF3 | 1440 | 0.063 | 0.470 | 0 | 1.35 | 1.07E−01 | NA | 5.03 | 2.26E−20 | 7.16E−18 |
| LIF | 3976 | 0.063 | 0.615 | 0 | 0.02 | 8.49E−01 | 9.58E−01 | 1.31 | 7.66E−31 | 4.05E−28 |
| MMP2 | 4313 | 0.063 | 0.615 | 0 | 0.08 | 7.11E−01 | 9.14E−01 | 0.08 | 5.19E−01 | 8.86E−01 |
| NFKB2 | 4791 | 0.063 | 0.482 | 0 | −0.16 | 1.08E−01 | 5.15E−01 | 1.01 | 6.47E−20 | 1.97E−17 |
| ADAMTS1 | 9510 | 0 | 0 | 0 | −0.49 | 7.73E−01 | NA | 1.14 | 1.42E−01 | 6.16E−01 |
| ADAMTS17 | 170691 | 0 | 0 | 0 | NA | NA | NA | 0.38 | 8.29E−01 | NA |
| IGFBP5 | 3488 | 0 | 0 | 0 | 0.21 | 6.94E−01 | NA | −1.61 | 4.68E−01 | NA |
| IL7R | 3575 | 0 | 0 | 0 | 3.09 | 3.36E−02 | NA | 0.84 | 7.17E−04 | 2.63E−02 |
| NMX3-1 | 4824 | 0 | 0 | 0 | 0.06 | 7.24E−01 | 9.20E−01 | 0.54 | 4.62E−02 | 3.91E−01 |
| PDGFB | 5155 | 0 | 0 | 0 | −0.21 | 1.68E−01 | 5.93E−01 | 1.01 | 1.71E−08 | 2.17E−06 |

Data for all the nodes in the network analysis (Fig. 3e and Fig. 7a and 7b) are shown here. The list is ranked by degree centrality.

TABLE 6

Results of network analysis for A549 and NHBE

| Genes entity | neme | #cDEG | A549 #DEG | FDR | #cDEG | NHBE #DEG | FDR |
|---|---|---|---|---|---|---|---|
| Predicted as Activated | 6773 | STAT2 | 14 | 4 | 1.06E−12 | 16 | 16 | 8.18E−13 |
| | 2353 | FOS | 2 | 2 | 1.66E−01 | 5 | 6 | 2.62E−02 |
| | 6774 | STAT3 | 4 | 4 | 6.52E−02 | 12 | 16 | 2.10E−03 |
| Protected as Inhibited | 3565 | IL4 | 2 | 2 | 3.16E−01 | 12 | 16 | 1.08E−04 |
| | 3596 | IL13 | 1 | 2 | 6.36E−01 | 7 | 10 | 1.14E−02 |
| | 3586 | IL10 | 3 | 3 | 1.60E−02 | 14 | 15 | 1.44E−09 |

A gene from the network (Fig. 7a) is predicted to be activated or inhibited based on the exressions of its downstream differentially expressed (DE) target genes, and the regulatory interactions (activation or inhibition) between it and its DE target genes. The number of DE target genes (#cDEG) that have the sign of their log2 fold changes consistent with the type of regulatory interaction (ex. when the interaction is activation and the target DEG is upregulated, then it increases the likelihood of this upstream regulator is activated), the total number of DEG measured (#DEG), and the false discovery rate (FDR) are shown here.

To further elucidate the concept, cytokines can be induced or downregulated with anti-androgen therapies thereby creating a pro-inflammatory environment. Creating this environment facilitates the introduction of immunotherapy in late-stage settings where tumors are typically cold.

The data presented in Table 7 confirms basal levels of cytokines and validates the findings. For example, cytokine IL6 was significantly higher in NSCLC than normal lung cells.

TABLE 7

Levels of Cytokines in Non-Small Cell Lung Cancer (NSCLC) and Normal Lung Cells

| | Gender | pg/mL | sCD40L | EGF | CCL1 | FGF-2 | FLT-3L |
|---|---|---|---|---|---|---|---|
| NSCLC | | | | | | | |
| A549 | Male | Avg | 1.07 | 1.15 | 1.175 | 14.295 | 0.115 |
| | | Std err | 0.74 | 1.15 | 1.175 | 14.295 | 0.005 |
| ALK-A549 | Male | Avg | 1.07 | 0.72 | 1.41 | 7.075 | 0.08 |
| | | Std err | 0.74 | 0.72 | 0.3 | 7.075 | 0.01 |
| H2030 | Male | Avg | 6.735 | 3.45 | 2.385 | 32.175 | 0.18 |
| | | Std err | 0.195 | 0.32 | 0.695 | 16.375 | 0.04 |
| H2030BrM | Male | Avg | 2.955 | 1.88 | 1.725 | 7.87 | 0.13 |
| | | Std err | 0.605 | 0.07 | 0.475 | 7.87 | 0.02 |
| PC9 | Male | Avg | 0.33 | 0 | 0 | 0 | 0.005 |
| | | Std err | 0.33 | 0 | 0 | 0 | 0.005 |
| PC9BrM | Male | Avg | 2.21 | 0.415 | 0.85 | 3.79 | 0.01 |
| | | Std err | 0.14 | 0.415 | 0.85 | 3.79 | 0.01 |
| H3122 | Male | Avg | 2.78 | 0 | 0.78 | 13.64 | 0.12 |
| | | Std err | 0.88 | 0 | 0.23 | 0 | 0.015 |
| UW-Lung2 | Female | Avg | 4.44 | 2.35 | 1.07 | 16.01 | 0.19 |
| | | Std err | 0.265 | 0.19 | 0.065 | 2.25 | 0 |
| UW-Lung16 | Male | Avg | 9.06 | 3.3 | 3.02 | 31.5 | 0.31 |
| | | Std err | 0.915 | 0.41 | 0.075 | 1.015 | 0.015 |
| Normal Lung | | | | | | | |
| HBEC3-KT | Female | Avg | 1.175 | 0 | 2.295 | 0 | 0.52 |
| | | Std err | 1.175 | 0 | 0.195 | 0 | 0.1 |
| hTERT Lung Fibroblast | Female | Avg | 2.47 | 0.985 | 1.1 | 0 | 0.04 |
| | | Std err | 0.4 | 0.985 | 0.61 | 05 | 0.01 |
| HULEC-5a | Male | Avg | 2.085 | 849.415 | 3.15 | 28.95 | 0.245 |
| | | Std err | 2.085 | 624.015 | 0.3 | 21.37 | 0.095 |
| HSAEC1-KT | Male | Avg | 4.635 | 0 | 3.085 | 0 | 0.245 |
| | | Std err | 2.555 | 0 | 1.645 | 0 | 0.125 |

TABLE 7-continued

Levels of Cytokines in Non-Small Cell Lung Cancer
(NSCLC) and Normal Lung Cells

| | Gender | pg/mL | CX3CL1 | G-CSF | GM-CSF | CXCL1 | IFN-α2 |
|---|---|---|---|---|---|---|---|
| NSCLC | | | | | | | |
| A549 | Male | Avg | 0 | 0 | 0.19 | 15.705 | 2.475 |
| | | Std err | 0 | 0 | 0.19 | 3.245 | 0.185 |
| ALK-A549 | Male | Avg | 0 | 0 | 1.55 | 16.835 | 0.835 |
| | | Std err | 0 | 0 | 0.3 | 3.125 | 0.835 |
| H2030 | Male | Avg | 7.46 | 0 | 2.28 | 27.45 | 4.96 |
| | | Std err | 4.96 | 0 | 0.68 | 1.19 | 0.51 |
| H2030BrM | Male | Avg | 6.775 | 0 | 0.875 | 19.095 | 3.11 |
| | | Std err | 1.435 | 0 | 0.085 | 5.105 | 0.69 |
| PC9 | Male | Avg | 2.67 | 0 | 0 | 13.87 | 1.09 |
| | | Std err | 2.67 | 0 | 0 | 2.54 | 1.09 |
| PC9BrM | Male | Avg | 0 | 0 | 0 | 13.775 | 0 |
| | | Std err | 0 | 0 | 0 | 1.615 | 0 |
| H3122 | Male | Avg | 5.69 | 0 | 6.26 | 19.6 | 1.11 |
| | | Std err | 2.705 | 0 | 0.685 | 1.52 | 0.275 |
| UW-Lung2 | Female | Avg | 8.07 | 0 | 79.35 | 175.59 | 1.63 |
| | | Std err | 2.23 | 0 | 4.385 | 6.405 | 0.25 |
| UW-Lung16 | Male | Avg | 13.8 | 20.82 | 683.24 | 1189.55 | 6.03 |
| | | Std err | 1.705 | 0.635 | 29.365 | 9.945 | 0.175 |
| Normal Lung | | | | | | | |
| HBEC3-KT | Female | Avg | 6.21 | 119.245 | 13.12 | 417.65 | 0 |
| | | Std err | 6.21 | 42.305 | 0.74 | 86.24 | 0 |
| hTERT Lung Fibroblast | Female | Avg | 0 | 0.145 | 0 | 35.935 | 0.525 |
| | | Std err | 0 | 0.145 | 0 | 7.865 | 0.055 |
| HULEC-5a | Male | Avg | 6.02 | 0.83 | 1.91 | 330.325 | 1.265 |
| | | Std err | 6.02 | 0.83 | 1.91 | 60.135 | 0.405 |
| HSAEC1-KT | Male | Avg | 11.71 | 711.865 | 0.095 | 105.63 | 1.71 |
| | | Std err | 11.71 | 135.525 | 0.095 | 6.14 | 1.71 |

| | Gender | pg/mL | IFNγ | IL-1α | IL-1β | IL-IRA | IL-2 |
|---|---|---|---|---|---|---|---|
| NSCLC | | | | | | | |
| A549 | Male | Avg | 0.09 | 0.185 | 0.175 | 0.09 | 0.04 |
| | | Std err | 0.05 | 0.185 | 0.175 | 0.09 | 0.04 |
| ALK-A549 | Male | Avg | 0.07 | 0.295 | 0 | 0.07 | 0.06 |
| | | Std err | 0.06 | 0.295 | 0 | 0.07 | 0.06 |
| H2030 | Male | Avg | 0.595 | 0 | 0.965 | 0.165 | 0.26 |
| | | Std err | 0.135 | 0 | 0.755 | 0.165 | 0.16 |
| H2030BrM | Male | Avg | 0.275 | 0 | 0.235 | 0.205 | 0.105 |
| | | Std err | 0.035 | 0 | 0.235 | 0.205 | 0.015 |
| PC9 | Male | Avg | 0.06 | 0 | 0 | 0.15 | 0 |
| | | Std err | 0.06 | 0 | 0 | 0.15 | 0 |
| PC9BrM | Male | Avg | 0.09 | 0 | 0 | 0.055 | 0 |
| | | Std err | 0.05 | 0 | 0 | 0.055 | 0 |
| H3122 | Male | Avg | 0.12 | 0 | 0 | 0 | 0.13 |
| | | Std err | 0.005 | 0.045 | 0.76 | 0.05 | 0 |
| UW-Lung2 | Female | Avg | 0.24 | 0 | 0 | 0 | 0.15 |
| | | Std err | 0.075 | 0.005 | 0.36 | 0.095 | 0.015 |
| UW-Lung16 | Male | Avg | 0.84 | 0 | 0.56 | 0 | 0.33 |
| | | Std err | 0.07 | 0.14 | 0.48 | 0.075 | 0.005 |
| Normal Lung | | | | | | | |
| HBEC3-KT | Female | Avg | 0.285 | 452.205 | 0 | 0.11 | 0.03 |
| | | Std err | 0.055 | 76.035 | 0 | 0.11 | 0.03 |
| hTERT Lung Fibroblast | Female | Avg | 0.08 | 0 | 0.585 | 0.11 | 0.035 |
| | | Std err | 0.07 | 0 | 0.585 | 0.11 | 0.035 |
| HULEC-5a | Male | Avg | 0.015 | 0.055 | 0.93 | 0.13 | 0.11 |
| | | Std err | 0.015 | 0.055 | 0.93 | 0.13 | 0.11 |
| HSAEC1-KT | Male | Avg | 0.05 | 57.79 | 0.885 | 5.51 | 0.045 |
| | | Std err | 0.01 | 4.46 | 0.885 | 4.86 | 0.045 |

TABLE 7-continued

Levels of Cytokines in Non-Small Cell Lung Cancer (NSCLC) and Normal Lung Cells

| | Gender | pg/mL | IL-3 | IL-4 | IL-5 | IL-6 | IL-7 |
|---|---|---|---|---|---|---|---|
| NSCLC | | | | | | | |
| A549 | Male | Avg | 0.01 | 0.255 | 0.05 | 12.85 | 0 |
| | | Std err | 0.01 | 0.025 | 0.04 | 0.985 | 0 |
| ALK-A549 | Male | Avg | 0 | 0.41 | 0 | 22.065 | 0 |
| | | Std err | 0 | 0.02 | 0 | 4.265 | 0 |
| H2030 | Male | Avg | 0.13 | 0.475 | 0.02 | 4630.29 | 0 |
| | | Std err | 0.13 | 0.055 | 0.02 | 96.085 | 0 |
| H2030BrM | Male | Avg | 0.03 | 0.13 | 0.02 | 675.17 | 0 |
| | | Std err | 0.03 | 0.01 | 0.01 | 36.805 | 0 |
| PC9 | Male | Avg | 0 | 0.195 | 0.01 | 24.015 | 0 |
| | | Std err | 0 | 0.035 | 0 | 4.995 | 0 |
| PC9BrM | Male | Avg | 0.03 | 0.39 | 0.01 | 56.39 | 0 |
| | | Std err | 0.03 | 0.02 | 0 | 8.23 | 0 |
| H3122 | Male | Avg | 0.08 | 0.94 | 0.01 | 12.6 | 0.16 |
| | | Std err | | 0.045 | 0.025 | 0.01 | 0.45 | 0.025 |
| UW-Lung2 | Female | Avg | 0.28 | 0.39 | 0.01 | 391.41 | 1.44 |
| | | Std err | 0.08 | 0.035 | 0.01 | 23.315 | 0.005 |
| UW-Lung16 | Male | Avg | 0.17 | 1.36 | 0.03 | 1951.37 | 0.26 |
| | | Std err | 0.01 | 0.075 | 0.005 | 269.535 | 0.025 |
| Normal Lung | | | | | | | |
| HBEC3-KT | Female | Avg | 0.01 | 0.815 | 0 | 11.9 | 0 |
| | | Std err | 0.01 | 0.015 | 0 | 2.11 | 0 |
| hTERT Lung Fibroblast | Female | Avg | 0 | 0.04 | 0.005 | 136.335 | 0 |
| | | Std err | 0 | 0 | 0.005 | 34.005 | 0 |
| HULEC-5a | Male | Avg | 0.11 | 0.035 | 0.015 | 15 | 0 |
| | | Std err | 0.09 | 0.015 | 0.015 | 3.35 | 0 |
| HSAEC1-KT | Male | Avg | 0 | 0.04 | 0.055 | 1.485 | 0 |
| | | Std err | 0 | 0.04 | 0.045 | 0.015 | 0 |

| | Gender | pg/mL | CXCL8 | IL-9 | IL-10 | IL-12p40 | IL-12p70 |
|---|---|---|---|---|---|---|---|
| NSCLC | | | | | | | |
| A549 | Male | Avg | 87.68 | 1.03 | 0.195 | 3.745 | 0.155 |
| | | Std err | 6.89 | 0.43 | 0.105 | 0.155 | 0.135 |
| ALK-A549 | Male | Avg | 97.775 | 0.21 | 0.22 | 0.91 | 0.06 |
| | | Std err | 11.325 | 0.05 | 0.08 | 0.08 | 0.01 |
| H2030 | Male | Avg | 1289.87 | 1.51 | 0.25 | 8.31 | 0.27 |
| | | Std err | 37.605 | 0.07 | 0.15 | 0.15 | 0.04 |
| H2030BrM | Male | Avg | 592.54 | 0.915 | 0.2 | 3.955 | 0.055 |
| | | Std err | 9.16 | 0.265 | 0.13 | 0.315 | 0.055 |
| PC9 | Male | Avg | 572.645 | 0.08 | 0.14 | 0.11 | 0.01 |
| | | Std err | 87.745 | 0.08 | 0.14 | 0.11 | 0.01 |
| PC9BrM | Male | Avg | 653.49 | 0.21 | 0.12 | 0.9 | 0.01 |
| | | Std err | 135.3 | 0.21 | 0.12 | 0.1 | 0.01 |
| H3122 | Male | Avg | 382.18 | 0.68 | 0.18 | 1.05 | 0 |
| | | Std err | 5.6 | 0.15 | 0.09 | 0.275 | 0.03 |
| UW-Lung2 | Female | Avg | 617.16 | 0.45 | 0.09 | 0.07 | 0.01 |
| | | Std err | 53.645 | 0.07 | 0.085 | 0.89 | 0.02 |
| UW-Lung16 | Male | Avg | 3405.7 | 1.48 | 0.29 | 9.04 | 0.2 |
| | | Std err | 716.42 | 0.145 | 0.07 | 1.305 | 0.055 |
| Normal Lung | | | | | | | |
| HBEC3-KT | Female | Avg | 409.31 | 0 | 0.195 | 0.34 | 0.11 |
| | | Std err | 62.28 | 0 | 0.165 | 0.08 | 0.11 |
| hTERT Lung Fibroblast | Female | Avg | 1025.795 | 0 | 0.16 | 0.185 | 0.115 |
| | | Std err | 109.785 | 0 | 0.14 | 0.185 | 0.045 |
| HULEC-5a | Male | Avg | 245.45 | 0.765 | 0.015 | 0.95 | 0 |
| | | Std err | 18.97 | 0.215 | 0.015 | 0 | 0 |
| HSAEC1-KT | Male | Avg | 28.48 | 1.015 | 0.535 | 2.165 | 0.225 |
| | | Std err | 0.64 | 0.305 | 0.205 | 2.165 | 0.115 |

TABLE 7-continued

Levels of Cytokines in Non-Small Cell Lung Cancer (NSCLC) and Normal Lung Cells

|  | Gender | pg/mL | IL-13 | IL-15 | IL-17A | IL-17E | IL17F |
|---|---|---|---|---|---|---|---|
| NSCLC | | | | | | | |
| A549 | Male | Avg | 2.31 | 0.68 | 0.125 | 0.45 | 0.155 |
|  |  | Std err | 1.06 | 0.02 | 0.125 | 0.45 | 0.155 |
| ALK-A549 | Male | Avg | 2.15 | 0.545 | 0.085 | 0.195 | 0.225 |
|  |  | Std err | 1.54 | 0.125 | 0.085 | 0.195 | 0.225 |
| H2030 | Male | Avg | 5.71 | 3.375 | 0.435 | 1.345 | 0.66 |
|  |  | Std err | 0.21 | 0.425 | 0.385 | 0.115 | 0.66 |
| H2030BrM | Male | Avg | 1.18 | 0.84 | 0.105 | 0.075 | 0.355 |
|  |  | Std err | 1.18 | 0.05 | 0.105 | 0.075 | 0.355 |
| PC9 | Male | Avg | 0.47 | 0.28 | 0.03 | 0 | 0.155 |
|  |  | Std err | 0.47 | 0.02 | 0.03 | 0 | 0.155 |
| PC9BrM | Male | Avg | 2.17 | 0.385 | 0 | 0 | 0.085 |
|  |  | Std err | 2.17 | 0.085 | 0 | 0 | 0.085 |
| H3122 | Male | Avg | 9.31 | 0.52 | 0.39 | 0.72 | 2 |
|  |  | Std err | 1.97 | 0 | 0.25 | 0.18 | 0.055 |
| UW-Lung2 | Female | Avg | 3.72 | 1.81 | 0.56 | 1.2 | 2.16 |
|  |  | Std err | 0.165 | 0.03 | 0.065 | 0.475 | 0 |
| UW-Lung16 | Male | Avg | 14.29 | 5.06 | 1.33 | 3.02 | 2.51 |
|  |  | Std err | 0.385 | 0.335 | 0.03 | 0.04 | 0.025 |
| Normal Lung | | | | | | | |
| HBEC3-KT | Female | Avg | 9.825 | 2.77 | 0.105 | 0.885 | 0.355 |
|  |  | Std err | 1.485 | 0.07 | 0.105 | 0.045 | 0.355 |
| hTERT Lung Fibroblast | Female | Avg | 0.17 | 0.385 | 0.105 | 0 | 0.225 |
|  |  | Std err | 0.17 | 0.175 | 0.105 | 0 | 0.225 |
| HULEC-5a | Male | Avg | 0.78 | 0.215 | 0.645 | 0.625 | 0.96 |
|  |  | Std err | 0.78 | 0.185 | 0.535 | 0.625 | 0.96 |
| HSAEC1-KT | Male | Avg | 1.96 | 0.285 | 0.58 | 4.66 | 0.82 |
|  |  | Std err | 1.96 | 0.285 | 0.58 | 1.12 | 0.82 |

|  | Gender | pg/mL | IL18 | IL22 | IL-27 | IP-10 | CCL2 |
|---|---|---|---|---|---|---|---|
| NSCLC | | | | | | | |
| A549 | Male | Avg | 0.115 | 2.375 | 0 | 0.735 | 1666.08 |
|  |  | Std err | 0.045 | 0.685 | 0 | 0.575 | 88.61 |
| ALK-A549 | Male | Avg | 0.05 | 7.54 | 0 | 0.365 | 202.045 |
|  |  | Std err | 0.02 | 4.14 | 0 | 0.365 | 24.485 |
| H2030 | Male | Avg | 0.42 | 17.02 | 22.985 | 1.35 | 6093.25 |
|  |  | Std err | 0.1 | 2.95 | 7.235 | 0.29 | 587.065 |
| H2030BrM | Male | Avg | 0.25 | 0 | 5.385 | 1.215 | 3853.63 |
|  |  | Std err | 0.04 | 0 | 5.385 | 0.475 | 1068.52 |
| PC9 | Male | Avg | 0.03 | 0 | 0 | 0 | 0.275 |
|  |  | Std err | 0 | 0 | 0 | 0 | 0.275 |
| PC9BrM | Male | Avg | 0.125 | 3.99 | 7.6 | 0 | 0.445 |
|  |  | Std err | 0.035 | 2.3 | 7.6 | 0 | 0.445 |
| H3122 | Male | Avg | 0 | 14.4 | 16.59 | 0 | 0.97 |
|  |  | Std err | 0.01 | 2.125 | 2.255 | 0 | 0.035 |
| UW-Lung2 | Female | Avg | 0.07 | 4.13 | 11.33 | 0 | 0.84 |
|  |  | Std err | 0.015 | 4.735 | 3.34 | 0 | 0.03 |
| UW-Lung16 | Male | Avg | 1.44 | 27.42 | 21.92 | 2.84 | 2401.98 |
|  |  | Std err | 0.105 | 1.39 | 1.285 | 0.025 | 9.37 |
| Normal Lung | | | | | | | |
| HBEC3-KT | Female | Avg | 0 | 21.17 | 22.03 | 0 | 0.115 |
|  |  | Std err | 0 | 0.83 | 6.28 | 0 | 0.115 |
| hTERT Lung Fibroblast | Female | Avg | 0 | 0 | 0 | 0 | 0.35 |
|  |  | Std err | 0 | 0 | 0 | 0 | 0.06 |
| HULEC-5a | Male | Avg | 0.045 | 0 | 0 | 0.605 | 63.415 |
|  |  | Std err | 0.025 | 0 | 0 | 0.605 | 8.315 |
| HSAEC1-KT | Male | Avg | 0.14 | 18.2 | 6.42 | 3.59 | 0.805 |
|  |  | Std err | 0.08 | 1.7 | 6.42 | 0.29 | 0.495 |

TABLE 7-continued

Levels of Cytokines in Non-Small Cell Lung Cancer (NSCLC) and Normal Lung Cells

|  | Gender | pg/mL | CCL7 | M-CSF | CCL22 | CXCL9 | CCL3 |
|---|---|---|---|---|---|---|---|
| NSCLC | | | | | | | |
| A549 | Male | Avg | 2.985 | 17.79 | 0.01 | 0.33 | 1.915 |
| | | Std err | 0.215 | 3.39 | 0.01 | 0.33 | 1.915 |
| ALK-A549 | Male | Avg | 1.13 | 81.31 | 0.005 | 0.35 | 2.285 |
| | | Std err | 1.13 | 0.99 | 0.005 | 0.35 | 2.285 |
| H2030 | Male | Avg | 3.445 | 14.625 | 0.08 | 0.595 | 3.12 |
| | | Std err | 0.675 | 3.525 | 0.04 | 0.425 | 3 |
| H2030BrM | Male | Avg | 0.97 | 7.745 | 0.065 | 0.38 | 2.425 |
| | | Std err | 0.97 | 0.375 | 0.035 | 0.37 | 2.425 |
| PC9 | Male | Avg | 0 | 8.735 | 0.1 | 0.34 | 1.55 |
| | | Std err | 0 | 1.855 | 0.06 | 0.34 | 1.55 |
| PC9BrM | Male | Avg | 1.265 | 10.22 | 0.05 | 0.37 | 1.665 |
| | | Std err | 1.265 | 2.36 | 0.05 | 0.37 | 1.665 |
| H3122 | Male | Avg | 2.07 | 8.73 | 4.25 | 0.66 | 0 |
| | | Std err | 0.44 | 0 | 0.145 | 0.02 | 0.22 |
| UW-Lung2 | Female | Avg | 1.47 | 233.81 | 0.05 | 0.82 | 0 |
| | | Std err | 0.135 | 7.72 | 0.005 | 0.055 | 0.61 |
| UW-Lung16 | Male | Avg | 5.42 | 152.6 | 12.74 | 0.98 | 2.93 |
| | | Std err | 0.61 | 0.17 | 0.545 | 0.02 | 0.07 |
| Normal Lung | | | | | | | |
| HBEC3-KT | Female | Avg | 2.535 | 11.705 | 0.03 | 0.95 | 1.705 |
| | | Std err | 0.865 | 2.945 | 0.03 | 0.61 | 1.705 |
| hTERT Lung Fibroblast | Female | Avg | 0 | 17.54 | 0.005 | 0.33 | 0.385 |
| | | Std err | 0 | 2.88 | 0.005 | 0.33 | 0.385 |
| HULEC-5a | Male | Avg | 1.4 | 8.925 | 0.01 | 0.095 | 1.89 |
| | | Std err | 0.2 | 3.135 | 0.01 | 0.075 | 1.89 |
| HSAEC1-KT | Male | Avg | 3.02 | 9.78 | 0.005 | 2.785 | 0 |
| | | Std err | 0.18 | 2 | 0.005 | 0.385 | 0 |

|  | Gender | pg/mL | CCL4 | PDGF-AA | PDGF-AB | CCL5 | TGFα |
|---|---|---|---|---|---|---|---|
| NSCLC | | | | | | | |
| A549 | Male | Avg | 0 | 78.02 | 2.105 | 0.63 | 0.055 |
| | | Std err | 0 | 9.32 | 2.105 | 0.06 | 0.055 |
| ALK-A549 | Male | Avg | 0 | 55.795 | 2.605 | 1.785 | 1.3 |
| | | Std err | 0 | 5.985 | 2.605 | 0.015 | 0.04 |
| H2030 | Male | Avg | 0 | 69.585 | 9.585 | 4.46 | 1.125 |
| | | Std err | 0 | 7.645 | 9.585 | 0.6 | 0.475 |
| H2030BrM | Male | Avg | 0 | 66.485 | 1.19 | 0.61 | 0.175 |
| | | Std err | 0 | 6.325 | 1.19 | 0.01 | 0.175 |
| PC9 | Male | Avg | 0 | 2.49 | 0 | 0.21 | 0.455 |
| | | Std err | 0 | 0.56 | 0 | 0.04 | 0.435 |
| PC9BrM | Male | Avg | 0 | 2.74 | 0 | 0.15 | 0.77 |
| | | Std err | 0 | 0.65 | 0 | 0.05 | 0.12 |
| H3122 | Male | Avg | 0 | 39.11 | 22.35 | 0.16 | 10.87 |
| | | Std err | 0 | 2.3 | 4.19 | 0.015 | 0.125 |
| UW-Lung2 | Female | Avg | 0 | 50.87 | 0 | 0.26 | 1.52 |
| | | Std err | 0 | 1.58 | 0 | 0.04 | 0.09 |
| UW-Lung16 | Male | Avg | 0 | 81.36 | 38 | 15.43 | 1.46 |
| | | Std err | 0 | 0.225 | 3.045 | 0.315 | 0.025 |
| Normal Lung | | | | | | | |
| HBEC3-KT | Female | Avg | 0 | 388.63 | 5.625 | 0.21 | 38.97 |
| | | Std err | 0 | 37.83 | 5.625 | 0 | 8.2 |
| hTERT Lung Fibroblast | Female | Avg | 0 | 13.035 | 0 | 0.445 | 0 |
| | | Std err | 0 | 0.535 | 0 | 0.025 | 0 |
| HULEC-5a | Male | Avg | 0 | 105.105 | 0 | 536.52 | 3.88 |
| | | Std err | 0 | 27.435 | 0 | 38.63 | 1.36 |
| HSAEC1-KT | Male | Avg | 0 | 89.35 | 0 | 0.16 | 0.875 |
| | | Std err | 0 | 14.29 | 0 | 0.1 | 0.425 |

TABLE 7-continued

Levels of Cytokines in Non-Small Cell Lung Cancer (NSCLC) and Normal Lung Cells

| | Gender | pg/mL | TNFα | TNFβ | VEGF-A | CCL24 | CCL8 |
|---|---|---|---|---|---|---|---|
| NSCLC | | | | | | | |
| A549 | Male | Avg | 0.285 | 1.61 | 65.475 | 0.93 | 0 |
| | | Std err | 0.135 | 0.43 | 8.715 | NA | NA |
| ALK-A549 | Male | Avg | 0.605 | 2.47 | 114.415 | 1.27 | 0 |
| | | Std err | 0.055 | 0.22 | 10.225 | NA | NA |
| H2030 | Male | Avg | 8.875 | 10.375 | 115.145 | 0 | 0 |
| | | Std err | 0.325 | 0.375 | 9.265 | NA | NA |
| H2030BrM | Male | Avg | 4.24 | 2.66 | 19.635 | 0 | 1.26 |
| | | Std err | 0.27 | 0.44 | 2.075 | NA | NA |
| PC9 | Male | Avg | 0.565 | 1.225 | 62.9 | 0 | 0 |
| | | Std err | 0.175 | 0.035 | 8.12 | NA | NA |
| PC9BrM | Male | Avg | 1.08 | 2.675 | 122.525 | 0 | 0 |
| | | Std err | 0 | 0.385 | 12.885 | NA | NA |
| H3122 | Male | Avg | 2.04 | 7.63 | 285.78 | 0.98 | 0.57 |
| | | Std err | 0.11 | 0.025 | 7.625 | 0.46 | 0.505 |
| UW-Lung2 | Female | Avg | 4.33 | 4.97 | 104.04 | 0.59 | 0.01 |
| | | Std err | 0.07 | 0.325 | 2.895 | 0.245 | 2.68 |
| UW-Lung16 | Male | Avg | 15.77 | 21.63 | 426.91 | 25.47 | 0.31 |
| | | Std err | 0.815 | 0.135 | 4.58 | 2.39 | 0.28 |
| Normal Lung | | | | | | | |
| HBEC3-KT | Female | Avg | 1.32 | 8.38 | 438.535 | 0 | 0 |
| | | Std err | 0.14 | 1 | 13.325 | NA | NA |
| hTERT Lung Fibroblast | Female | Avg | 1.045 | 0.9 | 10.345 | 0 | 0.55 |
| | | Std err | 0.135 | 0.24 | 2.625 | NA | NA |
| HULEC-5a | Male | Avg | 0.6 | 0.17 | 0 | 0 | 0.85 |
| | | Std err | 0.6 | 0.03 | 0 | NA | NA |
| HSAEC1-KT | Male | Avg | 0.54 | 0.39 | 6.025 | 0 | 0 |
| | | Std err | 0.44 | 0.08 | 0.875 | NA | NA |

| | Gender | pg/mL | CXCL13 | CCL13 | CCL1 | IL-16 | CCL17 |
|---|---|---|---|---|---|---|---|
| NSCLC | | | | | | | |
| A549 | Male | Avg | 0.02 | 0 | 0.03 | 0 | 0.08 |
| | | Std err | NA | NA | NA | NA | NA |
| ALK-A549 | Male | Avg | 0 | 0 | 0.02 | 0 | 0.06 |
| | | Std err | NA | NA | NA | NA | NA |
| H2030 | Male | Avg | 0.06 | 0 | 0.02 | 2.07 | 0.04 |
| | | Std err | NA | NA | NA | NA | NA |
| H2030BrM | Male | Avg | 0 | 0 | 0.01 | 0 | 0.04 |
| | | Std err | NA | NA | NA | NA | NA |
| PC9 | Male | Avg | 0.1 | 0 | 0.01 | 0 | 0.02 |
| | | Std err | NA | NA | NA | NA | NA |
| PC9BrM | Male | Avg | 0.05 | 0 | 0 | 2.07 | 0 |
| | | Std err | NA | NA | NA | NA | NA |
| H3122 | Male | Avg | 0.27 | 0 | 0 | 4.16 | 0.43 |
| | | Std err | 0.03 | 0 | 0 | 0.34 | 0.085 |
| UW-Lung2 | Female | Avg | 0.27 | 0 | 0 | 2.1 | 0 |
| | | Std err | 0.03 | 0 | 0 | 0.345 | 0 |
| UW-Lung16 | Male | Avg | 0.37 | 2.29 | 0 | 3.3 | 0 |
| | | Std err | 0.085 | 2.73 | 0 | 0.17 | 0.01 |
| Normal Lung | | | | | | | |
| HBEC3-KT | Female | Avg | 0.01 | 0 | 0 | 0 | 0 |
| | | Std err | NA | NA | NA | NA | NA |
| hTERT Lung Fibroblast | Female | Avg | 0 | 1.28 | 0 | 0 | 0 |
| | | Std err | NA | NA | NA | NA | NA |
| HULEC-5a | Male | Avg | 0 | 4.9 | 0 | 0 | 0 |
| | | Std err | NA | NA | NA | NA | NA |
| HSAEC1-KT | Male | Avg | 0.02 | 0 | 0.03 | 0 | 0 |
| | | Std err | NA | NA | NA | NA | NA |

TABLE 7-continued

Levels of Cytokines in Non-Small Cell Lung Cancer (NSCLC) and Normal Lung Cells

|  | Gender | pg/mL | CCL21 | CCL26 | LIF | TPO | SCF |
|---|---|---|---|---|---|---|---|
| NSCLC | | | | | | | |
| A549 | Male | Avg | 0 | 0 | 2.79 | 0 | 0.07 |
|  |  | Std err | NA | NA | NA | NA | NA |
| ALK-A549 | Male | Avg | 0 | 0 | 2.07 | 0 | 0.22 |
|  |  | Std err | NA | NA | NA | NA | NA |
| H2030 | Male | Avg | 0 | 0 | 10.59 | 0 | 2.34 |
|  |  | Std err | NA | NA | NA | NA | NA |
| H2030BrM | Male | Avg | 0 | 0 | 1.7 | 0 | 0 |
|  |  | Std err | NA | NA | NA | NA | NA |
| PC9 | Male | Avg | 0 | 0 | 3.68 | 0 | 0 |
|  |  | Std err | NA | NA | NA | NA | NA |
| PC9BrM | Male | Avg | 0 | 0 | 13.15 | 0 | 0.97 |
|  |  | Std err | NA | NA | NA | NA | NA |
| H3122 | Male | Avg | 23.02 | 0 | 27.73 | 8.24 | 1.34 |
|  |  | Std err | 17.645 | 0 | 0.765 | 3.97 | 0.3 |
| UW-Lung2 | Female | Avg | 21.9 | 0 | 9.44 | 16.18 | 2.14 |
|  |  | Std err | 6.985 | 0 | 2.12 | 1.325 | 0.3 |
| UW-Lung16 | Male | Avg | 63.9 | 0 | 5.22 | 7.58 | 4.83 |
|  |  | Std err | 2.6 | 0 | 0.04 | 3.31 | 0.99 |
| Normal Lung | | | | | | | |
| HBEC3-KT | Female | Avg | 0 | 0 | 0 | 0 | 2.24 |
|  |  | Std err | NA | NA | NA | NA | NA |
| hTERT Lung Fibroblast | Female | Avg | 0 | 0 | 25.42 | 0 | 0.22 |
|  |  | Std err | NA | NA | NA | NA | NA |
| HULEC-5a | Male | Avg | 0 | 0 | 0 | 0 | 0 |
|  |  | Std err | NA | NA | NA | NA | NA |
| HSAEC1-KT | Male | Avg | 0 | 0 | 0 | 0 | 0 |
|  |  | Std err | NA | NA | NA | NA | NA |

|  | Gender | pg/mL | TSLP | IL-33 | IL-20 | IL-21 | IL-23 |
|---|---|---|---|---|---|---|---|
| NSCLC | | | | | | | |
| A549 | Male | Avg | 0 | 0.43 | 0 | 0.3 | 12.98 |
|  |  | Std err | NA | NA | NA | NA | NA |
| ALK-A549 | Male | Avg | 0 | 0.43 | 0 | 0.52 | 16.23 |
|  |  | Std err | NA | NA | NA | NA | NA |
| H2030 | Male | Avg | 0 | 0 | 0 | 0 | 6.48 |
|  |  | Std err | NA | NA | NA | NA | NA |
| H2030BrM | Male | Avg | 0 | 0 | 94 | 0 | 6.48 |
|  |  | Std err | NA | NA | NA | NA | NA |
| PC9 | Male | Avg | 0 | 0 | 0 | 0.07 | 0 |
|  |  | Std err | NA | NA | NA | NA | NA |
| PC9BrM | Male | Avg | 0 | 0 | 0 | 0.29 | 0 |
|  |  | Std err | NA | NA | NA | NA | NA |
| H3122 | Male | Avg | 0.15 | 0.31 | 0 | 0 | 16.56 |
|  |  | Std err | 0.115 | 0 | 3.58 | 0 | 5.155 |
| UW-Lung2 | Female | Avg | 0 | 0 | 29 | 0 | 7.33 |
|  |  | Std err | 0 | 0.48 | 18.485 | 0 | 4.09 |
| UW-Lung16 | Male | Avg | 0.08 | 0.04 | 0.25 | 0 | 16.56 |
|  |  | Std err | 0.06 | 0 | 25.85 | 0 | 3.095 |
| Normal Lung | | | | | | | |
| HBEC3-KT | Female | Avg | 0 | 0 | 0 | 0 | 0 |
|  |  | Std err | NA | NA | NA | NA | NA |
| hTERT Lung Fibroblast | Female | Avg | 0 | 0.96 | 0 | 0.6 | 0 |
|  |  | Std err | NA | NA | NA | NA | NA |
| HULEC-5a | Male | Avg | 0 | 0 | 45.72 | 0 | 6.48 |
|  |  | Std err | NA | NA | NA | NA | NA |
| HSAEC1-KT | Male | Avg | 0 | 0.43 | 45.72 | 0 | 25.21 |
|  |  | Std err | NA | NA | NA | NA | NA |

TABLE 7-continued

Levels of Cytokines in Non-Small Cell Lung Cancer (NSCLC) and Normal Lung Cells

|  | Gender | pg/mL | TRAIL | CCL27 | CXCL12 | CXCL5 | CCL15 | IL-28A |
|---|---|---|---|---|---|---|---|---|
| NSCLC | | | | | | | | |
| A549 | Male | Avg | 0.2 | 0.04 | 0 | 970.66 | 0 | 0 |
|  |  | Std err | NA | NA | NA | NA | NA | NA |
| ALK-A549 | Male | Avg | 0.09 | 0 | 0 | 1750.7 | 0 | 0.09 |
|  |  | Std err | NA | NA | NA | NA | NA | NA |
| H2030 | Male | Avg | 0.17 | 0 | 0 | 4.44 | 0 | 0.42 |
|  |  | Std err | NA | NA | NA | NA | NA | NA |
| H2030BrM | Male | Avg | 0 | 0.14 | 0 | 0 | 0 | 0.76 |
|  |  | Std err | NA | NA | NA | NA | NA | NA |
| PC9 | Male | Avg | 0 | 0 | 0 | 0 | 0 | 0 |
|  |  | Std err | NA | NA | NA | NA | NA | NA |
| PC9BrM | Male | Avg | 0.03 | 0 | 0 | 4.44 | 0 | 0.59 |
|  |  | Std err | NA | NA | NA | NA | NA | NA |
| H3122 | Male | Avg | 0.14 | 0.07 | 70 | 4.85 | 13.19 | 0.38 |
|  |  | Std err | 0.015 | 0.065 | 13.545 | 1.405 | 1.37 | 0.295 |
| UW-Lung2 | Female | Avg | 0.14 | 0 | 59.42 | 0 | 8.69 | 0.9 |
|  |  | Std err | 0.015 | 0.04 | 3.73 | 0 | 1.175 | 0.515 |
| UW-Lung16 | Male | Avg | 0.11 | 0.18 | 47.43 | 2532.48 | 7.32 | 1.49 |
|  |  | Std err | 0.01 | 0.035 | 8.715 | 186.035 | 0.195 | 0.665 |
| Normal Lung | | | | | | | | |
| HBEC3-KT | Female | Avg | 0 | 0 | 0 | 0 | 0 | 0 |
|  |  | Std err | NA | NA | NA | NA | NA | NA |
| hTERT Lung Fibroblast | Female | Avg | 0.12 | 0 | 0 | 10.16 | 0 | 0 |
|  |  | Std err | NA | NA | NA | NA | NA | NA |
| HULEC-5a | Male | Avg | 0.03 | 0 | 0 | 1.61 | 0 | 0 |
|  |  | Std err | NA | NA | NA | NA | NA | NA |
| HSAEC1-KT | Male | Avg | 0 | 0 | 0 | 4.44 | 0 | 0 |
|  |  | Std err | NA | NA | NA | NA | NA | NA |

At least one sample has more than 1 pg/mL of these cytokines:

NSCLC: sCD40L, EGF, CCL11, FGF-2, CX3CL1, GM-CSF, CXCL1, IFN-α2, IL-6, CXCL8, IL9, IL-12p40, IL-13, IL-15, IL-22, IL-27, CCL2, CCL7, M-CSF, CCL3, PDGF-AA, PDGF-AB, CCL5, TGFα, TGFβ, VEGF-A, LIF, TPO, SCF, IL-20, IL23, CXCL12, CXCL5, CCL15

Normal lung: sCD40L, EGF, CCL11, FGF-2, CX3CL1, G-CSF, GM-CSF, CXCL1, IFN-α2, IL-1α, IL-1RA, IL-6, CXCL8, IL9, IL-13, IL-15, IL-22, IL27, CCL2, CCL7, M-CSF, CCL3, PDGF-AA, CCL5, TGFα, TGFβ, VEGF-A, LIF, IL-20, IL-23, CXCL5, CCL15

B. Materials and Methods

AR Gene Expression in Normal Lung

Normalized transcript data from 427 lung tissues was extracted from the publicly available Human Protein Atlas (http://www.proteinatlas.org). Data originated from the Genotype-Tissue Expression project (https://gtexportal.org), which collects and analyzes multiple human postmortem tissues. RNA-seq data from lung tissues was mapped based on RSEMv1.2.22 (v7) and the resulting transcripts per million values were normalized as described (https://www.proteinatlas.org/about/assays+annotation).

Cell Culture and Treatment

A549 (CCL-185) and NCI-H2228 (CRL-5935) cells were obtained from ATCC. Both cell lines were cultured in RPMI 1640 medium supplemented with 5% (v/v) charcoal-stripped fetal bovine serum (FBS, GeminiBio) and maintained in humidified incubator at 37° C. and 5% $CO_2$ for at least 48 h prior to any treatment. After pre-conditioned in medium with charcoal-stripped FBS, cells were treated with either 1 nM R1881 (Metribolone, Sigma), 5 μM Enzalutamide (MDV3100, APExBIO), or combinations of both (one group was pre-treated with Enzalutamide for 30 min prior to induction of R1881, while the other group was pre-treated with R1881 for 30 min prior to Enzalutamide treatment). For AR siRNA, three different siRNA sequences (termed siAR1 to 3) were designed to target AR mRNA (Integrated DNA Technologies). Based on the effectiveness of each sequence, the inventors used the combination of siAR2 and siAR3 (50% each, at 10 nM concentration and 48 h transfection time) for all the siRNA treatment in this study. Lipofectamine RNAiMAX reagent (Thermo) was used for transfection following manufacturer's instruction, and scrambled siRNA was served as control.

```
siAR1 sequences:
                                    (SEQ ID NO: 1)
GUCACAAAGAUUUCUUACCAACUCT (Fwd);

(SEQ ID NO: 2)
AGAGUUGGUAAGAAAUCUUUGUGACUA (Rev)

siAR2 sequences:
                                    (SEQ ID NO: 3)
CUUUUGACCUGCUAAUCAAGUCACA (Fwd);

(SEQ ID NO: 4)
UGUGACUUGAUUAGCAGGUCAAAGUG (Rev)

siAR3 sequences:
                                    (SEQ ID NO: 5)
AUGAAAGCACUGCUACUCUUCAGCA (Fwd);

(SEQ ID NO: 6)
UGCUGAAGAGUAGCAGUGCUUUCAUGC (Rev)
```

After treatment of enzalutamide at various concentrations (range from 0.5 µM to 200 µM) for 24 h, 48 h, and 72 h, the cell viabilities of lung cancer cell lines were determined by using PrestoBlue Cell Viability Reagent (Thermo). Relative fluorescence units (RFU) were measured with CLARIOstar Plus microplate reader (BMG Labtech, Software version: 5.21 R2, Firmware version: 1.15), with excitation wavelength set at 535 nm and emission at 590 nm. The raw absorbance values were first subtracted by the averaged absorbance value of background control (medium only). Then, the cell survival rate at each concentration was calculated by normalizing to the signal of vehicle control samples. The data was curve fitted using the sigmoidal dose-response equation (Y=Bottom+(Top−Bottom)/(1+10^((Log IC50−X)*Hill Slope)) in OriginLab software (version 2017, OriginLab) to determine the EC50 values.

Quantitative Real-Time PCR (qRT-PCR)

From two independent biological experiments with 3 replicates (n=6), RNA samples were collected with TRIzol reagent (Invitrogen) and isolated using RNeasy Mini Kit (Qiagen). RNA concentrations were measured using A260 nm/A280 nm spectroscopy on the Nanodrop ND-1000 (Thermo-scientific). For each RNA sample, 1000 ng of RNA was reversed transcribed into first-strand cDNA using the High-Capacity RNA-to-cDNA Kit (Applied Biosystems).

AR mRNA expressions of A549 and NCI-H2228 cells after R1881 and/or enzalutamide treatment were measured by using the Power SYBR Green Master Mix (Applied Biosystems) and Bio-Rad C1000 qPCR Detection System. Three independent biological replicates of mRNA samples were collected for each condition, and three technical replicates were run for each sample in qRT-PCR. The fold changes and p-values were calculated with the ΔΔCt method32 and two-sample t-test, respectively. Ubiquitin C (UBC) was used as the housekeeping gene for normalization.

```
AR primers:
                                 (SEQ ID NO: 7)
AGTACTGAATGACAGCCATCTG (Fwd);

(SEQ ID NO: 8)
CAACAACCAGCCCGACT (Rev)

UBC primers:
                                 (SEQ ID NO: 9)
CCTTATCTTGGATCTTTGCCTTG (Fwd);

(SEQ ID NO: 10)
GATTTGGGTCGCAGTTCTTG (Rev)
```

Changes in expression levels of AR signaling genes were screened using Bio-Rad's PrimePCR pathway 384-well panel: Androgen Receptor Signaling SAB target list (Cat #10047228) and Androgen Receptor Nuclear Signaling (Cat #10025068). Relative mRNA levels were determined via qRT-PCR by using the Bio-Rad C1000 qPCR Detection System and SsoAdvanced Universal SYBR Green Supermix (Cat #172-5271, Bio-Rad) as suggested by manufacturer's protocol. Two independent biological replicates of mRNA samples were collected for each condition, and one reaction was run for each sample. If necessary, additional technical replicates were run to rule out any outlier. Relative mRNA expressions and p-values were calculated using the ΔΔCt method and two-sample t-test in Bio-Rad CFX Maestro program (version: 4.0.2325.0418). GAPDH, HPRT1, and TBP were selected as housekeeping genes for normalization, while untreated sample (cultured in medium with charcoal-stripped FBS) served as control for the other three treatment groups (treatment of R1881 for 24 h, Enzalutamide treatment for 24 h, and 48 h of AR siRNA transfection). The stabilities of housekeeping genes were checked using the geNorm algorithm provided in CFX Maestro. M values of all housekeeping genes used in this study are less than 0.5, which is considered ideal. Log 2-transformed expression levels and −log 10 (p-value) of all treatment groups were plotted as Bubble and Color map graph in the Origin 2020 software.

Immunofluorescent Imaging and Quantification

The lung cancer cells were cultured on coverslips (#1.5 thickness, 18 mm×18 mm) and treated with R1881 for 24 h, Enzalutamide for 24 h, combination of Enzalutamide/R1881 for 24 h, or AR siRNA for 48 h. The samples were then fixed with 4% paraformaldehyde/1×PBS for 10 minutes, permeabilized with 0.5% Triton X-100/1×PBS for 5 minutes, and finally wash in 0.2% Tween-20/1×PBS solution for 5 minutes. After incubating in blocking buffer (5% normal goat serum and 0.2% fish skin gelatin in 0.2% Tween/PBS) for 1 hour at room temperature, the cells were stained with primary antibodies overnight at 4° C. The primary antibodies include Anti-Androgen Receptor monoclonal rabbit antibody (5153S, Cell Signaling Technologies) and Anti-α-Tubulin monoclonal mouse antibody (T6074, Sigma-Aldrich) at 1:500 dilution in blocking buffer. Next day, samples were stained with 1:500 dilution of Donkey anti-Rabbit Alexa Fluor 594 (A21207, Invitrogen) and Goat anti-Mouse Alexa Fluor 488 (A11029, Invitrogen) for 1 hour, and then incubated in DRAQ5 solution (1:10,000, Thermo Scientific) for 20 minutes before mounting the coverslip. Immunofluorescence images were captured on Leica TCS WLL SP8 Laser scanning confocal microscopy (Leica Microsystems) using 63× oil immersion objective (Scale bar: 10 µm). Multiple images were taken at different fields of coverslip to obtain at least 100 cells for AR quantification. The sum of pixel intensities of AR signal within the nucleus and cytoplasm was quantified using a custom MATLAB program (R2017b, MathWorks). Briefly, the program utilized the actin and DRAQ5 channels to create masks for the cytoplasm and nucleus regions, respectively. These masks were then used to determine the AR signal within cytoplasm and nucleus, and the nucleus-to-cytoplasm ratio of AR signal was calculated by dividing the AR signal inside the nucleus by the AR signal within the entire cell (nucleus and cytoplasm).

Statistical Analyses of A549 and NHBE Cell Lines RNA-Seq Data

Raw sequencing data of SARS-CoV-2 treated and control samples from A549 and NHBE cell lines in Blanco-Melo et al. 2020 were downloaded from GEO (GEO accession: GSE147507). A reference genome was manually built by combining GRCh38.p13 from RefSeq with SARS-CoV-2 (GenBank accession: NC 045512.2), respiratory syncytial virus (GenBank accession: NC_001803.1), and influenza A virus (GenBank accession: AF389115.1-AF389122.1) genomes. Quality control of single-end sequencing files was conducted using FastQC v0.11.7.

Reads were aligned using STAR v2.7.1a. The gene-by-sample count matrix was calculated using RSEM v1.3.0. Genes with average expression less than 1 were filtered out. Differential expression (DE) analyses were performed between SARS-CoV-2 treated and control samples from A549 and NHBE separately using DESeq2 v1.24.0 (Love et al., 2014) under R v4.0.0. P-values were adjusted via Benjamini-Hochberg for multiple tests. Those genes with adjusted p-value less than or equal to 0.05 and absolute value of log 2 fold change greater or equal to 0.6 were selected as significant DE genes.

Gene Set Enrichment Analysis (GSEA), Gene Ontology (GO) and Network Analysis

GSEA software (v4.0.3 for Windows) was used to perform enrichment analysis on the A549 and NHBE RNA sequencing data. All genes were included in the analysis. The default settings in the software, which includes phenotype permutation, weighted enrichment statistic, and signal-to-noise metric for ranking genes, were used. The GSEA was run with the Hallmark gene sets (H collection v7.1) from the Molecular Signatures Database (MSigDB), and gene sets with false discovery rate less than 0.25 were considered enriched.

The network analysis for the Bio-Rad's 384-well AR signaling gene expression data and the RNA-seq data sets from the Blanco-Melo et al. 2020 study were done by using Advaita Bio's iPathwayGuide (version 1910, https://www.advaitabio.com/ipathwayguide). All measured gene expressions from the Bio-Rad's AR signaling panel were imported into the iPathwayGuide platform, and the network for each treatment condition was constructed by including all differentially expressed genes (DEGs) as input nodes. Integrating one intermediate gene between any two input nodes (genes) was allowed so that the inventors could further explore the relationships of these genes. In addition, some gene nodes were manually added for easier comparison between Enzalutamide (AR) and AR siRNA (IL6 and MAF) treated cells. For the public COVID-19 data sets, the DEGs of NHBE cells from the JAK-STAT signaling pathway (KEGG) along with some genes of interest (IL6, IL6R, IL6ST, AR, FOS, STAT3, ADAMTS1, ADAMTS17, TGFB1, MAF, NKX3-1, MMP2, IGFBP5, SOCS3, NFKB1, NFKB2) were used to build the gene interaction networks. In addition, one intermediate gene between two input nodes was also included. Only regulatory interactions (activation and inhibition) and interactions with high confidence (score>700) were considered in this study. Any isolated node (gene) was hidden in the final diagram. Upstream regulator analysis was also done in iPathwayGuide. The prediction for activated or inhibited genes were calculated based on the interactions with their downstream DEGs, and the p-values were adjusted via Benjamini-Hochberg method to control the false discovery rate (FDR).

GO term results were generated by iPathwayGuide. The p-values of GO terms were corrected using the Elim pruning method, which emphasize the most specific term first. Shared Biological Processes that are significant in both A549 and NHBE RNA-seq data were extracted, and the GO terms related to immune response and inflammatory response were plotted in FIG. 3a.

Data and Code Availability

RNA-seq data from published study were downloaded from GEO (GEO accession: GSE147507).

Other embodiments and uses of the invention will be apparent to those skilled in the art from consideration from the specification and practice of the invention disclosed herein. All references cited herein for any reason, including all journal citations and U.S./foreign patents and patent applications, are specifically and entirely incorporated herein by reference. It is understood that the invention is not confined to the specific reagents, formulations, reaction conditions, etc., herein illustrated and described, but embraces such modified forms thereof as come within the scope of the following claims.

The sequence listing txt file in computer readable form, named "3152.376_ST25", having a size of 3 KB and created on Feb. 17, 2022, is incorporated by reference herein.

REFERENCES

1. Baratchian, M. et al. No evidence that androgen regulation of pulmonary TMPRSS2 explains sex-discordant COVID-19 outcomes. bioRxiv, 2020.2004.2021.051201, doi:10.1101/2020.04.21.051201 (2020).
2. Cai, C. et al. Androgen receptor gene expression in prostate cancer is directly suppressed by the androgen receptor through recruitment of lysine-specific demethylase 1. Cancer Cell 20, 457-471, doi:10.1016/j.ccr.2011.09.001 (2011).
3. Tran, C. et al. Development of a second-generation antiandrogen for treatment of advanced prostate cancer. Science (New York, N.Y.) 324, 787-790, doi:10.1126/science.1168175 (2009).
4. Ueda, T., Bruchovsky, N. & Sadar, M. D. Activation of the Androgen Receptor N-terminal Domain by Interleukin-6 via MAPK and STAT3 Signal Transduction Pathways. Journal of Biological Chemistry 277, 7076-7085 (2002).
5. Handle, F. et al. SOCS3 Modulates the Response to Enzalutamide and Is Regulated by Androgen Receptor Signaling and CpG Methylation in Prostate Cancer Cells. doi:10.1158/1541-7786.MCR-15-0495 (2016).
6. Ho, I. C., Hodge, M. R., Rooney, J. W. & Glimcher, L. H. The Proto-Oncogene c-maf Is Responsible for Tissue-Specific Expression of Interleukin-4. Cell 85, 973-983, doi:https://doi.org/10.1016/S0092-8674(00)81299-4 (1996).
7. Bao, K. & Reinhardt, R. L. The differential expression of IL-4 and IL-13 and its impact on type-2 Immunity. Cytokine 75, 25-37, doi:10.1016/j.cyto.2015.05.008 (2015).
8. Fuseini, H. et al. Testosterone Decreases House Dust Mite-Induced Type 2 and IL-17A-Mediated Airway Inflammation. The Journal of Immunology 201, 1843, doi:10.4049/jimmunol.1800293 (2018).
9. de Vries, J. E. The role of IL-13 and its receptor in allergy and inflammatory responses. Journal of Allergy and Clinical Immunology 102, 165-169, doi:10.1016/50091-6749(98)70080-6 (1998).
10. Szczepanik, A. M., Funes, S., Petko, W. & Ringheim, G. E. IL-4, IL-10 and IL-13 modulate Aβ(1-42)-induced cytokine and chemokine production in primary murine microglia and a human monocyte cell line. Journal of Neuroimmunology 113, 49-62, doi:https://doi.org/10.1016/S0165-5728(00)00404-5 (2001).
11. Jevnikar, Z. et al. Epithelial IL-6 trans-signaling defines a new asthma phenotype with increased airway inflammation. J Allergy Clin Immunol 143, 577-590, doi:10.1016/j.jaci.2018.05.026 (2019).
12. Ruwanpura, S. M. et al. Therapeutic Targeting of the IL-6 Trans-Signaling/Mechanistic Target of Rapamycin Complex 1 Axis in Pulmonary Emphysema. Am J Respir Crit Care Med 194, 1494-1505, doi:10.1164/rccm.201512-23680C (2016).
13. Marini, M., Vittori, E., Hollemborg, J. & Mattoli, S. Expression of the potent inflammatory cytokines, granulocyte-macrophage-colony-stimulating factor and interleukin-6 and interleukin-8, in bronchial epithelial cells of patients with asthma. J Allergy Clin Immunol 89, 1001-1009, doi:10.1016/0091-6749(92)90223-o (1992).
14. Hawkins, G. A. et al. The IL6R variation Asp(358)Ala is a potential modifier of lung function in subjects with asthma. J Allergy Clin Immunol 130, 510-515.e511, doi:10.1016/j.jaci.2012.03.018 (2012).
15. Maston, L. D. et al. in Pulm Circ Vol. 8 (2018).
16. Yokoyama, A. et al. Circulating interleukin-6 levels in patients with bronchial asthma. Am J Respir Crit Care Med 151, 1354-1358, doi:10.1164/ajrccm.151.5.7735584 (1995).
17. Broide, D. H. et al. Cytokines in symptomatic asthma airways. J Allergy Clin Immunol 89, 958-967, doi:10.1016/0091-6749(92)90218-q (1992).
18. Wang, J. et al. Soluble interleukin-6 receptor is elevated during influenza A virus infection and mediates the IL-6 and IL-32 inflammatory cytokine burst. Cellular & Molecular Immunology 12, 633-644, doi:10.1038/cmi.2014.80 (2015).
19. Zhang, C., Wu, Z., Li, J.-W., Zhao, H. & Wang, G.-Q. The cytokine release syndrome (CRS) of severe COVID-19 and Interleukin-6 receptor (IL-6R) antagonist Tocilizumab may be the key to reduce the mortality. International Journal of Antimicrobial Agents, 105954, doi: https://doi.org/10.1016/j.ijantimicag.2020.105954 (2020).
20. Coomes, E. A. & Haghbayan, H. Interleukin-6 in COVID-19: A Systematic Review and Meta-Analysis. medRxiv, 2020.2003.2030.20048058, doi:10.1101/2020.03.30.20048058 (2020).
21. Herold, T. et al. Level of IL-6 predicts respiratory failure in hospitalized symptomatic COVID-19 patients. medRxiv, 2020.2004.2001.20047381, doi:10.1101/2020.04.01.20047381 (2020).
22. Blanco-Melo, D. et al. SARS-CoV-2 launches a unique transcriptional signature from in vitro, ex vivo, and in vivo systems. bioRxiv, 2020.2003.2024.004655, doi:10.1101/2020.03.24.004655 (2020).
23. Schneider, W. M., Chevillotte, M. D. & Rice, C. M. Interferon-Stimulated Genes: A Complex Web of Host Defenses. Annual Review of Immunology 32, 513-545, doi:10.1146/annurev-immunol-032713-120231 (2014).
24. Markiewski, M. M. & Lambris, J. D. The Role of Complement in Inflammatory Diseases From Behind the Scenes into the Spotlight. The American Journal of Pathology 171, 715-727, doi:https://doi.org/10.2353/ajpath.2007.070166 (2007).
25. Liberzon, A. et al. The Molecular Signatures Database (MSigDB) hallmark gene set collection. Cell systems 1, 417-425, doi:10.1016/j.cels.2015.12.004 (2015).
26. Jones, S. A. & Jenkins, B. J. Recent insights into targeting the IL-6 cytokine family in inflammatory diseases and cancer. Nature Reviews Immunology 18, 773-789, doi:10.1038/s41577-018-0066-7 (2018).
27. Blanco-Melo, D. et al. Imbalanced Host Response to SARS-CoV-2 Drives Development of COVID-19. Cell 181, 1036-1045.e1039, doi:https://doi.org/10.1016/j.cell.2020.04.026 (2020).
28. Ng, C. T. et al. Gold nanoparticles induce serum amyloid A1-Toll-like receptor 2 mediated NF-kB signaling in lung cells in vitro. Chem Biol Interact 289, 81-89, doi:10.1016/j.cbi.2018.04.022 (2018).
29. Hahn, A. et al. Serum amyloid A1 mediates myotube atrophy via Toll-like receptors. J Cachexia Sarcopenia Muscle 11, 103-119, doi:10.1002/jcsm.12491 (2020).
30. Uhlen, M. et al. Proteomics. Tissue-based map of the human proteome. Science (New York, N.Y.) 347, 1260419, doi:10.1126/science.1260419 (2015).
31. The Genotype-Tissue Expression (GTEx) pilot analysis: Multitissue gene regulation in humans. Science (New York, N.Y.) 348, 648, doi:10.1126/science.1262110 (2015).
32. Schmittgen, T. D. & Livak, K. J. Analyzing real-time PCR data by the comparative CT method. Nature Protocols 3, 1101-1108, doi:10.1038/nprot.2008.73 (2008).
33. Vandesompele, J. et al. Accurate normalization of real-time quantitative RT-PCR data by geometric averaging of multiple internal control genes. Genome Biology 3, research0034.0031, doi:10.1186/gb-2002-3-7-research0034 (2002).
34. O'Leary, N. A. et al. Reference sequence (RefSeq) database at NCBI: current status, taxonomic expansion, and functional annotation. Nucleic Acids Res 44, D733-745, doi:10.1093/nar/gkv1189 (2016).
35. Andrews, S., Krueger, F., Seconds-Pichon, A., Biggins, F. & Wingett, S. FastQC: A quality control tool for high throughput sequence data. Babraham Institute (2015).
36. Dobin, A. et al. STAR: ultrafast universal RNA-seq aligner. Bioinformatics (Oxford, England) 29, 15-21, doi:10.1093/bioinformatics/bts635 (2012).
37. Li, B. & Dewey, C. N. RSEM: accurate transcript quantification from RNA-Seq data with or without a reference genome. BMC Bioinformatics 12, 323, doi:doi:10.1186/1471-2105-12-323 (2011).
38. Love, M. I., Huber, W. & Anders, S. in Genome Biol Vol. 15 (2014).
39. R: A Language and Environment for Statistical Computing (R Core Team, 2020).
40. Subramanian, A. et al. Gene set enrichment analysis: a knowledge-based approach for interpreting genome-wide expression profiles. Proceedings of the National Academy of Sciences of the United States of America 102, 15545-15550, doi:10.1073/pnas.0506580102 (2005).
41. Mootha, V. K. et al. PGC-1α-responsive genes involved in oxidative phosphorylation are coordinately downregulated in human diabetes. Nature genetics 34, 267-273, doi:10.1038/ng1180 (2003).
42. Draghici, S. et al. A systems biology approach for pathway level analysis. Genome Res 17, 1537-1545, doi:10.1101/gr.6202607 (2007).
43. Tarca, A. L. et al. A novel signaling pathway impact analysis. Bioinformatics (Oxford, England) 25, 75-82, doi:10.1093/bioinformatics/btn577 (2009).
44. Donato, M. et al. Analysis and correction of crosstalk effects in pathway analysis. Genome Res 23, 1885-1893, doi:10.1101/gr.153551.112 (2013).
45. Ahsan, S. & Draghici, S. Identifying Significantly Impacted Pathways and Putative Mechanisms with iPathwayGuide. Current Protocols in Bioinformatics 57, 7.15.11-17.15.30, doi:doi:10.1002/cpbi.24 (2017).

We claim:

1. A method of treating a lung inflammation in a subject infected with SARS-COV-2, comprising administering an effective amount of an Androgen Receptor (AR) antagonist to the subject via inhalation to target a respiratory tract;

inhibiting AR expression in the subject wherein the AR antagonist decreases IL6 expression and increases MAF expression in lung cells; and reducing lung inflammation in the subject;

wherein the AR antagonist promotes the expression of one or more checkpoint inhibitors selected from a group consisting of IL4 and IL 13 which are capable of inhibiting IL6 expression;

wherein the AR antagonist is administered at a dose of 80 mg to 240 mg per day.

2. The method of claim 1, wherein the AR antagonist is selected from a group consisting of enzalutamide, bicalutamide, apalutamide, flutamide, nilutamide, and darolutamide.

3. The method of claim 1, wherein the AR antagonist increases IL4 expression.

4. The method of claim 1, wherein the AR antagonist increases IL 13 expression.

5. The method of claim 1, wherein the AR antagonist is administered for a duration of less than seven days.

6. The method of claim 1, wherein the subject has COVID-19 and the lung inflammation comprises bronchial epithelial cells infected with SARS-COV-2.

7. The method of claim 1, wherein the subject has lung cancer and the lung inflammation comprises cells affected with lung cancer.

8. The method of claim 1, wherein the subject is a male.

* * * * *